United States Patent [19]
Cance et al.

[11] Patent Number: 6,015,893
[45] Date of Patent: Jan. 18, 2000

[54] OLIGONUCLEOSIDE COMPOUNDS AND METHODS FOR INHIBITING TUMOR GROWTH, INVASION AND METASTASIS

[75] Inventors: William G. Cance; Edison T. Liu; Lewis V. Owens, all of Chapel Hill, N.C.

[73] Assignee: The University of North Carolina at Chapel Hill, Chapel Hill, N.C.

[21] Appl. No.: 08/863,118

[22] Filed: May 27, 1997

Related U.S. Application Data

[63] Continuation of application No. 08/276,843, Jul. 18, 1994, abandoned.

[51] Int. Cl.$^7$ ..................................................... C07H 21/00
[52] U.S. Cl. ........................................................... 536/24.5
[58] Field of Search .................................... 536/24.1, 24.5

[56] References Cited

PUBLICATIONS

Andre et al., "Expression of an n-terminally truncated form of human focal adhesion kinase in brain", *Biochemical and Biophysical Research Communications* 190:140–147 (Jan. 1993).

Burridge et al., "Tyrosine Phosphorylation of Paxillin and pp125$^{FAK}$ Accompanies Cell Adhesion to Extracellular Matrix: A Role in Cytoskeletal Assembly", *The Journal of Cell Biology,* 119:4 893–903 (Nov. 1992).

Cance et al., "Novel Protein Kinases Expressed in Human Breast Cancer", *Int. J. Cancer:* 54:571–577 (Mar. 1993).

Chan et al., "In Vitro and in Vivo Consequences of VLA–2 Expression on Rhabdomyosarcoma Cells", *Science* 251:1600–1602 (Mar. 1991).

Cobb et al., "Stable of Association of pp60$^{src}$ and pp59$^{fyn}$ with the Focal Adhesion Protein Tyrosine Kinase, pp125$^{FAK}$", *Mo. Cell. Biol.,* 14:147–155 (Jan. 1994).

Ezzell C., "Just the FAK(s), Ma'am: Researchers Investigate A New Signaling Enzyme", *J. NIH Research* 5:49–54 (Dec. 1993).

Frisch, et al., "Disruption of Epithelial Cell–Matrix Interactions Induces Apoptosis", *J. Cell Biology,* 124:619–626 (Feb. 1994).

Gehlsen, et al., "Intergrin expression in human melanoma cells with differing invasive and metastatic properties", *Clin. Exp. Metastasis* 10:111–120 (Sep.—Nov. 1992).

Guan, et al., "Fibronectin/integrin interaction induces tyrosine phosphorylation of a 120–kDa protein", *clel Regulation* 2:951–964 (Nov. 1991).

Guan, J.L. & Shalloway, D., "Regulation of focal adhesion–associated protein tyrosine kinase by both cellular adhesion and oncogenic transformation", *Nature* 358:690–692 (Aug. 1992).

Hanks, et al., "Focal adhesion protein–tyrosine kinase phosphorylated in response to cell attachment to fibronectin", *Proc. Nat'l. Acad. Sci. USA* 89:8489–8491 (Sep. 1992).

Hildebrand, et al., "Identification of Sequences Required for the Efficient Localization of the Focal Adhesion Kinase pp125$^{FAK}$, to Cellular Focal Adhesions", *J. Cell Biol.* 123:993–1005 (Nov. 1993).

ILIC, et al., "Reduced cell motility and enhanced focal adhesion contact formation in cells from FAK–deficient mcie", *Nature* 377:539–544 (Oct. 1995).

Juliano, et al., "Adhesion Molecules in cancer: the role of integrins", *J.A. Curr. Opin. Cell Biol.* 5:812–818 (Oct. 1993).

Kornberg, et al., "Signal transduction by integrin: Increased protein tyrosine phosphorylation caused by clustering of $\beta_1$ integrins", *Proc. Nat'l. Acad. Sci. USA* 88:8392–8396 (Oct. 1991).

Kornberg, et al., "Cell Adhesion or Integrin Clustering Increases Phosphorylation of a Focal Adhesion–associated Tyrosine Kinase", *J. Biol. Chem.* 267:23439–442 (Nov. 1992).

Liotta, et al., "Cancer Metastasis and Angiogenesis: An Imbalance of Positive and Negative Regulation", *Cell* 64:327–336 (Jan. 1991).

Lipfert et al., "Integrin–dependent phosphorylation and activation of the protein tyrosine kinase pp125FAK in platelets", *Journal of Cell Biology* 119:4 905–912 (Nov. 1992).

Neckers et al., "Antisense technology: biological utility and practical considerations", *American Journal of Physiology* 9:1 L1–L12 (Jul. 1993).

Ruiz, et al., "Suppression of Mouse Melanoma Metastasis by EA–1, A Monoclonal Antibody Specific for α6 Integrins", *Cell Adhesion Commun.* 1;67–81 (1993).

Schaller, et al., "Autonomous Expression of a Noncatalytic Domain of the Focal Adhesion–Associated Protein Tyrosine Kinase pp125$^{FAK}$", *Mol. Cell Biol.* 13:785–791 (Feb. 1993).

Schaller et al., "pp125FAK, a structurally distinctive protein–tyrosine kinase associated with focal adhesions", *Proc. Natl. Acad. Sci. U.S.A.* 89:5192–5196 (Jun. 1992).

Talamonti, et al., "Increase in Activity and Level of pp60$^{c-src}$ in Progressive Stages of Human Colorectal Cancer", *J. Clin. Invest.* 91:53–60 (Jan. 1993).

Varner, et al., "Ectopic expression of integrin $\alpha^5\beta^1$ suppresses in vitro growth and tumorigenecity of human colon carcinoma cells", *Mol. Biol. Cell* 3:232A (Sep. 1992).

Weber, et al., "Differential pp60$^{c-src}$ Activity in Well and Poorly Differentiated Human Colon Carcinomas and Cell Lines", *J. Clin. Invest.* 90:815–821 (Sep. 1992).

Weiner et al., "Expression of focal adhesion kinase gene and invasive cancer", *The Lancet* 342:1024–1025 (Oct. 1993).

Weiner et al., "Expression of Growth Factor Receptors, the Focal Adhesion Kinase, and Other Tyrosine Kinases in Human Soft Tissue Tumors", *Ann. Surg. Oncol.* 1:18–27 (1994).

(List continued on next page.)

*Primary Examiner*—John S. Brusca
*Attorney, Agent, or Firm*—Myers Bigel Sibley & Sajovec

[57] ABSTRACT

Oligonucleoside compounds useful in inhibiting expression of focal adhesion kinase protein in animals, and related methods and formulations for reducing cancer cell growth, invasion and metastasis. The compounds are selected to be complementary to a target region of a focal adhesion kinase nucleic acid sequence, preferably human FAK mRNA.

15 Claims, 9 Drawing Sheets

PUBLICATIONS

Whitney et al., "human T and B lymphocytes express a structurally conserved focal adhesion kinase, pp125FAK", *DNA and Cell Biology* 12:9 823–827 (Nov. 1993).

Xing et al., "Direct interaction of v–Src with the focal adhesion kinase mediated by the Src SH2 domain", *Molecular Biology of the Cell* 5:413–421 (Apr. 1994).

Zachary, et al., "Focal Adhesion Kinase (p125$^{FAK}$): A Point of Convergence in the Action of Neuropeptides, Integrins, and Oncogenes", *Cell* 71:891–894 (Dec. 1992).

Zachary, et al., "Bombesin, vasopressin, and endothelin stimulation of tyrosine phosphorylation in swiss 3T3 cells", *J. Biol. Chem.* 267:19031–34 (Sep. 1992).

Amersham Catalog. Amersham Corporation pp. 28 and 259, 1992.

Awgulewitsch e tal. Spatial restriction in expression of a nouse homeo box locus within the central nervous system. Nature vol. 320 pp. 328–335, 1986.

Milner et al. Selecting effective antisense reagents on combinatorial oligonucelotide arrays. Nature Biotechnology vol. 15, pp. 537–541, 1997.

Wagner et al. Potent and selective inhibition of gene expression by an antisense heptanucleotide Nature Biotechnology vol. 14 840–844, 1996.

Uhlmann et al. Antisense oligonucleotides: A new therapeutic principle Chemical reviews vol. 90 543–584. 1990.

```
HUMFAK    1 MAAAYLDPNLNHTPNSSTKTHLGTGMERSPGAMERVLKVFHHFESSSEPTTWASIIRHGDATDVRGIIQKIVDSHKVKHV
MUSFAK    1 MAAAYLDPNLNHTPSSSTKTHLGTGMERSPGAMERVLKVFHHFESSSEPTTWASIIRHGDATDVRGIIQKIVDSHKVKHV
CHKFAK    1 MAAAYLDPNLNHTPSSSAKTHLGTGMERSPGAMERVLKVFHYFENSSEPTTWASIIRHGDATDVRGIIQKIVDCHKVKNV

HUMFAK   81 ACYGFRLSHLRSEEVHWLHVDMGVSSVREKYELAHPPEEWKYELRIRYLPKGFLNQFTEDKPTLNFFYQQVKSDYMQEIA
MUSFAK   81 ACYGFRLSHLRSEEVHWLHVDMGVSSVREKYELAHPPEEWKYELRIRYLPKGFLNQFTEDKPTLNFFYQQVKSDYMQEIA
CHKFAK   81 ACYGLRLSHLQSEEVHWLHLDMGVSNVREKFELAHPPEEWKYELRIRYLPKGFLNQFTEDKPTLNFFYQQVKNDYMLEIA

HUMFAK  161 DQVDQEIALKLGCLEIRRSYWEMRGNALEKKSNYEVLEKDVGLKRFFPKSLLDSVKAKTLRKLIQQTFRQFANLNREESI
MUSFAK  161 DQVDQEIALKLGCLEIRRSYWEMRGNALEKKSNYEVLEKDVGLKRFFPKSLLDSVKAKTLRKLIQQTFRQFANLNREESI
CHKFAK  161 DQVDQEIALKLGCLEIRRSYGEMRGNALEKKSNYEVLEKDVGLRRFFPKSLLDSVKAKTLRKLIQQTFRQFANLNREESI

FAK1AS       FAK2AS       recombinant peptide
HUMFAK  241 LKFFEILSPVYRFDKECFKCALGSSWIISVELAIGPEEGISYLTDKGCNPTHLADFTQVQTIQYSNSEDKDRKGMLQLKI
MUSFAK  241 LKFFEILSPVYRFDKECFKCALGSSWIISVELAIGPEEGISYLTDKGCNPTHLADFNQVQTIQYSNSEDKDRKGMLQLKI
CHKFAK  241 LKFFEILSPVYRFDKECFKCALGSSWIISVELAIGPEEGISYLTDKGANPTHLADFNQVQTIQYSNSEDKDRKGMLQLKI HUMFAK  321 AGAPEPLTVTAPSLTIAENMADLIDGYCRLVNGTSQSFIIRPQKEGERALPSIPKLANSEKQGMRTHAVSVSETDDYAEI
MUSFAK  321 AGAPEPLTVTAPSLTIAENMADLIDGYCRLVNGATQSFIIRPQKEGERALPSIPKLANSEKQGMRTHAVSVSETDDYAEI
CHKFAK  321 AGAPEPLTVTAPSLTIAENMADLIDGYCRLVNGATQSFIIRPQKEGERALPSIPKLANNEKQGVRSHTVSVSETDDYAEI kinase domain
HUMFAK  401 IDEEDTYTMPSTRDYEIQRERIE LGRCIGEGQFGDVHQGIYMSPENPALAVAIKTCKNCTSDSVREKFLQEALTMRQFDH
MUSFAK  401 IDEEDTYTMPSTRDYEIQRERIE LGRCIGEGQFGDVHQGVYLSPENPALAVAIKTCKNCTSDSVREKFLQEALTMRQFDH
CHKFAK  401 IDEEDTYTMPSTRDYEIQRERIE LGRCIGEGQFGDVHQGIYMSPENPAMAVAIKTCKNCTSDSVREKFLQEALTMRQFDH HUMFAK  481 PHIVKLIGVITENPVWIIMELCTLGELRSFLQVRKYSLDLASLILYAYQLSTALAYLESKRFVHRDIAARNVLVSSNDCV
MUSFAK  481 PHIVKLIGVITENPVWIIMELCTLGELRSFLQVRKYSLDLASLILYAYQLSTALAYLESKRFVHRDIAARNVLVSSNDCV
CHKFAK  481 PHIVKLIGVITENPVWIIMELCTLGELRSFLQVRKFSLDLASLILYAYQLSTALAYLESKRFVHRDIAARNVLVSATDCV HUMFAK  561 KLGDFGLSRYMEDSTYYKASKGKLPIKWMAPESINFRRFTSASDVWMFGVCMWEILMHGVK PFQGVKNNDVIGRIENGER
MUSFAK  561 KLGDFGLSRYMEDSTYYKASKGKLPIKWMAPESINFRRFTSASDVWMFGVCMWEILMHGVK PFQGVKNNDVIGRIENGER
CHKFAK  561 KLGDFGLSRYMEDSTYYKASKGKLPIKWMAPESINFRRFTSASDVWMFGVCMWEILMHGVK PFQGVKNNDVIGRIENGER
```

FIG. 1A

```
HUMFAK  641  LPMPPNCPPTLYSLMTKCWAYDPSRRPRFTELKAQLSTILEEEKAQQEERMRMESRRQATVSWDSGGSDEAPPKPSRPGY
MUSFAK  641  LPMPPNCPPTLYSLMTKCWAYDPSRRPRFTELKAQLSTILEEEKVQQEERMRMESRRQATVSWDSGGSDEAPPKPSRPGY
CHKFAK  641  LPMPPNCPPTLYSLMTKCWAYDPSRRPRFTELKAQLSTILEEEKLQQEERMRMESRRQVTVSWDSGGSDEAPPKPSRPGY

HUMFAK  721  PSPRSSEGFYPSPQHMVQTNHYQVSGYPGSHGITAMAGSIYPGQASLLDQTDSWNHRPQEIAMWQPNVEDSTVLDLRGIG
MUSFAK  721  PSPRSSEGFYPSPQHMVQTNHYQVSGYPGSHGIPAMAGSIYQGQASLLDQTELWNHRPQEMSMWQPSVEDSAALDLRGMG
CHKFAK  721  PSPRSSEGFYPSPQHMVQPNHYQVSGYSGSHGIPAMAGSIYPGQASLLDQTDSWNHRPQEVSAWQPNMEDSGTLDVRGMG

HUMFAK  801  QVLPTHLMEERLIRQQQEMEEDQRWLEKEERFL..KPDVRLSRGSIDREDGSLQGPIGNQHIYQPVGKPDPAAPPKKPPR
MUSFAK  801  QVLPPHLMEERLIRQQQEMEEDQRWLEKEERFL..KPDVRLSRGSIDREDGSFQGPTGNQHIYQPVGKPDPAAPPKKPPR
CHKFAK  801  QVLPTHLMEERLIRQQQEMEEDQRWLEKEERFLVMKPDVRLSRGSIEREDGGLQGPAGNQHIYQPVGKPDHAAPPKKPPR

HUMFAK  879  PGAPGHLGSLASLSSPADSYNEGVKLQPQEISPPPTANLDRSNDKVYENVTGLVKAVIEMSSKIQPAPPEEYVPMVKEVG
MUSFAK  879  PGAPGHLSNLSSISSPADSYNEGVKLQPQEISPPPTANLDRSNDKVYENVTGLVKAVIEMSSKIQPAPPEEYVPMVKEVG
CHKFAK  881  PGAP.HLGSLASLNSPVDSYNEGVKIKPQEISPPPTANLDRSNDKVYENVTGLVKAVIEMSSKIQPAPPEEYVPMVKEVG

HUMFAK  959  LALRTLLATVDETIPLLPASTHREIEMAQKLLNSDLGELINKMKLAQQYVMTSLQQEYKKQMLTAAHALAVDAKNLLDVI
MUSFAK  959  LALRTLLATVDETIPALPASTHREIEMAQKLLNSDLGELISKMKLAQQYVMTSLQQEYKKQMLTAAHALAVDAKNLLDVI
CHKFAK  960  LALRTLLATVDESLPVLPASTHREIEMAQKLLNSDLAELINKMKLAQQYVMTSLQQEYKKQMLTAAHALAVDAKNLLDVI

HUMFAK 1039  DQARLKMLGQTRPH
MUSFAK 1039  DQARLKMLGQTRPH
CHKFAK 1040  DQARLKMISQSRPH
```

FIG. 1B

OLIGONUCLEOSIDE COMPOUNDS AND METHODS FOR INHIBITING TUMOR GROWTH, INVASION AND METASTASIS

"This application is a continuation of copending application(s) Ser. No. 08/276,843 filed on Jul. 18, 1994, now abandoned."

FIELD OF THE INVENTION

This invention relates to antisense compounds useful in inhibiting the expression of focal adhesion kinase protein in animals and animal cells, and the use of such compounds in suppressing cancer cell growth, invasion and metastasis.

BACKGROUND

The invasion and metastasis of cancer is a complex process which involves changes in cell adhesion properties which allow a transformed cell to invade and migrate through the extracellular matrix (ECM) and acquire anchorage-independent growth properties. Liotta, L. A., et al., Cell 64:327–336 (1991). Some of these changes occur at focal adhesions, which are cell/ECM contact points containing membrane-associated, cytoskeletal, and intracellular signaling molecules. The molecules contained within a focal adhesion include cytoskeletal proteins such as actin, paxillin, and tensin; ECM proteins such as fibronectin, laminin, and vitronectin; cell surface receptors such as the integrins; and protein tyrosine kinases such as src family kinases and a recently described tyrosine kinase, the focal adhesion kinase, or FAK.

The FAK gene was originally isolated from chicken and mouse fibroblasts and codes for a unique 125 kD cytoplasmic protein tyrosine kinase ($p125^{FAK}$). Schaller, M. D., et al., Proc. Natl. Acad. Sci. USA 89:5192–5196 (1992); Hanks, S. K., et al., Proc. Natl. Acad. Sci. USA 89:8487–8491 (1992). The protein contains highly conserved consensus sequences within its tyrosine kinase domain, but is flanked by long amino-and carboxy-terminal sequences. It also lacks the src homology (SH2 and SH3) domains seen in the amino-terminal sequences of other cytoplasmic kinases. As FAK has begun to be characterized, a growing body of evidence suggests that FAK is a critical molecule in cell signaling events which regulate cell adhesion and motility, and may be of importance in the invasion and metastasis of cancer. Zachary, I. & Rozengurt, E., Cell 71:891–894 (1992). First of all, the activity of FAK is directly linked to the src oncogene. It has been demonstrated that $p125^{FAK}$ becomes phosphorylated, or activated, in cells which have been transformed with v-src, suggesting that FAK may play a role in the transformation by this oncogene. Recent data have shown that $p60^{src}$ stably associates with $p125^{FAK}$, and it is postulated that the SH2 domain of src protects FAK from dephosphorylation by phosphatases, resulting in its constitutive activation. Cobb, B. S., et al., Mol. Cell. Biol. 14:147–155 (1994). The linkage of FAK to src is particularly intriguing, since levels of c-src activity have been shown to be increased in invasive and metastatic tumors. Weber, T. K., et al., J. Clin. Invest. 90:815–821 (1992); Talamonti, M. S., et al., J. Clin. Invest. 91:53–60 (1993). This raises the possibility that FAK may be a major downstream mediator of the invasive and metastic process in human tumors.

Another unusual property of FAK which suggests a role in invasion and metastasis is its relationship to the integrins and integrin-mediated signaling pathways. The integrin family of cell surface receptors have been shown to mediate many of the adhesive interactions of tumors and are now thought to be actively involved in signal transduction processes. Juliano, R. L. & Varner, J. A., Curr. Opin. Cell Biol. 5:812–818 (1993). The integrin molecules are composed of noncovalently bound α and β subunits which link the cytoskeleton to the extracellular matrix by binding specific adhesion molecules such as fibronectin, talin, vinculin, and actin filaments. When cellular adhesion is mimicked by clustering integrin receptors with monoclonal antibodies or induced by plating cells on a fibronectin-coated substrata, increased phosphorylation of $p125^{FAK}$ has been demonstrated. Kornberg, L., et al., J. Biol. Chem. 267:23439–442 (1992).

Specific integrin expression patterns have been associated with both cellular proliferation and metastasis. For example, overexpression of the α5β1 integrin in human colon cancer cells has markedly reduced tumorigenicity in nude mice. Varner, J. A., et al., Mol. Biol. Cell 3:232A (1992). In contrast, other integrin expression patterns have been associated with invasion and metastasis, rather than cellular growth. Transfection of the α2β1 integrin into the RD rhabdomyosarcoma cells has markedly increased tumor metastases in nude mouse tail vein injection assays. Chan, B. M. C., et al., Science 251:1600–1602 (1991). Furthermore, expression of either the α6β4 laminin receptor or the αvβ3 integrin has been associated with metastatic behavior in studies of melanoma metastases. Ruiz, P., et al., Cell Adhesion Commun. 1:67–81 (1993), Gehlsen, K. R., et al., Clin. Exp. Metastasis 10:111–120 (1992). These findings further raise the possibility of a significant role for FAK in the metastatic process.

The final property of FAK which also suggests a link to cellular growth is its relationship to the growth stimulation of neuropeptides such as bombesin, vasopressin, and endothelin. These molecules exert mitogenic stimuli via receptors which are coupled to effectors via heterotrimeric G proteins. Stimulation of Swiss 3T3 cells with these neuropeptides has led to a rapid increase in specific $p125^{FAK}$ phosphorylation, suggesting that the effector molecules exert their stimuli via FAK. Zachary, I., et al., J. Biol. Chem. 267:19031–34 (1993). Thus, FAK appears to be a convergent pathway for growth stimulatory neuropeptides, transformation by the v-src oncogene, and integrin-mediated signaling.

Zachary, I. & Rozengurt, E., Cell 71:891–894 (1992).

SUMMARY OF THE INVENTION

The present invention relates to compositions and methods for inhibiting the growth, invasion and/or metastasis of tumors or cancer cells using antisense oligonucleoside compounds that are complementary to a portion of an FAK mRNA, preferably human FAK mRNA. The inventors have established that such antisense compounds are effective in inhibiting the expression of the FAK protein product in transformed (i.e. cancerous) human cells, and that such inhibition results in reduced cancer cell growth and adhesion, induction of cell apoptosis, reduced cell motility and invasiveness, reduced cell colony formation and anchorage-independent cell growth, and reduced rates of tumor formation.

The FAK antisense oligonucleoside compounds of the invention are chosen to have a length sufficient to bind to and inhibit the expression of the targeted FAK mRNA. The compounds may be of any suitable length, although typically they will have a sequence of from about 6 to about 40, and preferably about 12 to about 30, linked nucleosides. The nucleoside sequence is chosen to be complementary to a selected FAK mRNA target region sequence, such that the antisense compounds are capable of hybridizing to the selected FAK target region of the FAK mRNA within the subject cells and effecting inhibition of FAK expression. The individual nucleosides of the antisense compounds are linked by internucleoside bonding groups ("backbone" linkages) preferably chosen to afford the compounds stability against degradation by endogenous cellular nucleases, and also to enhance stable and specific hybridization to the target FAK mRNA. Such linkages may include natural phosphodiester linkages, but preferably will include one or more nuclease-resistant non-phosphodiester linkages such as phosphorothioate, phosphorodithioate, alkyl- or arylphosphonate, phosphoramidate, phosphotriester, alkyl- or arylphosphonothioate, aminoalkylphosphonate, aminoalkylphosphonothioate, phosphorofluoridate, boranophosphate, silyl, formacetal, thioformacetal, morpholino or peptide-based linkages. Specificity and binding affinity toward the target FAK mRNA may be increased through the use of chirally-selected asymmetric linkages, preferably Rp-chiral linkages.

The present antisense compounds may be constructed to achieve inhibition of FAK expression by a variety of different mechanisms. For example, the compounds may be designed to form a stable duplex with the RNA so as to block transcription at the ribosome. The duplex blocking mechanism is particularly usefully employed when targeting the 5'-untranslated portion or other non-coding regions of the target mRNA, or elsewhere in the mRNA if ribosomal displacement of the antisense compound does not occur to a significant extent. For target regions where ribosomal displacement is a consideration (e.g., in coding regions), increased duplex stability may be achieved by incorporating a cross-linking moiety in the antisense compound so as to link the hybridized antisense compound to the target mRNA. Alternatively, inhibition of FAK expression may be achieved by using antisense structures which disrupt the integrity or structure of the FAK mRNA molecule, as for example by mRNA cleavage. Cleavage of the target FAK mRNA may be accomplished by choosing antisense sequences capable of activating cellular RNase H or other endogenous cleavage agents, by incorporating a cleavage moiety in the antisense compound, or by co-administering a cleavage substance.

The FAK antisense oligonucleoside compounds of the invention may also be usefully derivatized or conjugated with, for example, 2'-sugar substituents, particularly electron-withdrawing groups which increase binding affinity; cellular-uptake or membrane-disruption moieties; intercalating agents; radical generators; alkylating agents; detectable labels; chelators; or the like.

The present invention further includes formulations comprising FAK antisense compounds for use in mammalian cancer therapy, and methods for using the same. The antisense compounds of the invention are also useful in the in vitro or ex vivo study of the biological properties of cancer and other mammalian cells, for example in studies of cell growth, invasion, and metastasis, and studies of the inhibition of such properties.

These and other aspects of the present invention are described in more detail in the following detailed description.

BRIEF DESCRIPTION OF THE DRAWINGS

FIGS. 1A-1B show the amino acid sequences for human (HUMAK) (SEQ ID NO:1), mouse (MUSFAK) (SEQ ID NO:2) and chicken (CHKFAK) (SEQ ID NO:3) focal adhesion kinase proteins, aligned to show sequence homology.

DETAILED DESCRIPTION

Figure 2:
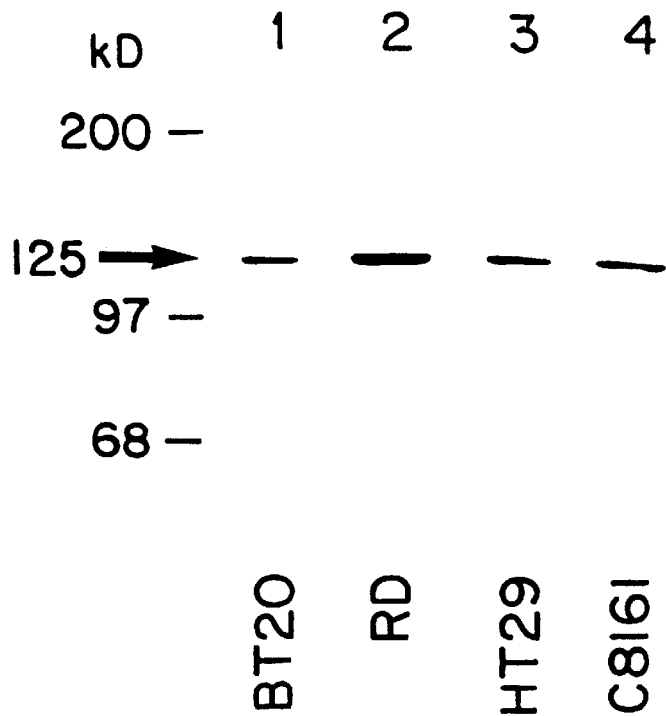
FIG. 2 is a Western blot analysis of $p125^{FAK}$ expression in RD (lane 1), BT20 (lane 2), HT29 (lane 3) and C8161 (lane 4) cell lines.

A. FAK Antisense Compounds of the Invention

FIG. 1 depicts an amino acid sequence for human FAK (labeled "HUMFAK" SEQ ID NO:1), as derived from a cDNA clone isolated from the human breast cancer cell line BT-20. See Example 2 below. This sequence represents 1052 amino acids of the human FAK sequence. The amino acid sequences for mouse ("MUSFAK" SEQ ID NO:2) and chicken ("CHKFAK" SEQ ID NO:3) FAK are also shown. The kinase domain of the respective molecules is boxed. The underlined "recombinant peptide" portion of HUMFAK corresponds to a 66-amino acid region (198 bp) that was subdloned and expressed as a fusion product and used for generation of polyclonal antibodies specific for human FAK (see Example 3 below).

FIG. 1 also shows two regions, labeled "FAK1AS" and "FAK2AS", which correspond to two FAK mRNA regions targeted for inhibition by complementary antisense oligonucleosides according to the present invention. As detailed in Examples 5A–5G below, such antisense compounds were shown to be effective in inhibiting cancer cell growth, cell adhesion, cell invasion, colony formation and tumor formation, and were effective in inducing cell apoptosis.

The FAK antisense compounds of the invention generally include a sequence of nucleosides that is chosen to be complementary to a target region of the target FAK nucleic acid strand, and particularly the human FAK mRNA strand, such that the antisense compound is capable of hybridizing to the target FAK nucleic acid and inhibiting expression thereof. The term "oligonucleoside" refers to a sequence of nucleoside units linked by internucleoside bonding groups ("backbone" linkages), and thus includes oligonucleotides (linked by phosphodiester backbone linkages) as well as nucleoside polymers linked by structures other than phosphodiester bonds. The term "complementary" refers to a sequence of oligonucleosides (or the individual nucleo side units therein), which is capable of forming hydrogen bonds, and thereby base pairing or hybridizing, with the base sequence of a target region of the target FAK nucleic acid to form a Watson-Crick or "double helix" type structure (whether or not actually helicized) or a portion thereof. Complementary sequences include those which have exact base-by-base complementarity to the target region of the target nucleic acid strand, and also includes oligonucleoside sequences which may lack a complement for one or more nucleotides in the target region, but which still have sufficient binding affinity for the target FAK sequence to form a hybridized structure within the subject (e.g., in vivo or intracellular) environment, so as to specifically recognize the target sequence and inhibit expression thereof. Complementary sequences also embrace oligonucleoside compounds, or pairs of distinct oligonucleoside compounds, which have sufficient complementarity to achieve triple-strand binding with a target FAK nucleic acid single-strand sequence, or with a double-strand portion of the target nucleic acid such as a hairpin loop structure, thereby to inhibit FAK expression in the subject environment.

The target FAK nucleic acid sequence is preferably FAK mRNA, including FAK pre-mRNA. The particular target region may be chosen from a variety of locations in the coding or non-coding portions of the mRNA molecule. Suitable non-coding regions include the 5'-untranslated region, the initiation codon region, the 5'-cap site region, splice acceptor or donor sites, intron branch sites, or polyadenylation regions. Where the target region is a non-coding region, inhibition of protein production can be achieved prior to the translation process by suitable hybridization of the antisense oligonucleoside, and ribosomal displacement of the hybridized oligonucleoside generally does not occur during attempted translation. In such cases translation may be blocked by the effect of complementary hybridization alone, and it will generally not be necessary to incorporate additional inhibition structures (e.g., cross-linking or cleavage moieties) into the antisense compound. Pre-mRNA splicing as a target for antisense oligonucleosides is discussed in R. Kole et al., Advanced Drug Delivery Reviews, 6:271–286 (1991). Where the target region is in the coding portion of the FAK mRNA, it is believed that ribosomal displacement of the antisense compound may sometimes occur during the translation process. In such instances it is usefull to incorporate cross-linking, cleavage, RNase H activating or other expression inhibition structures into the antisense compound in order to increase efficacy. Such structures are described in more detail below. The target region, and the associated sequence of complementary nucleosides in the antisense compound, should be selected such that hybridization is specific to the intended FAK target, thus avoiding or minimizing hybridization with non-FAK nucleic acid sequences in the genome of the subject cell or animal that are not intended to be inhibited. In this regard, publicly-available computer listings of gene sequences may be checked so as to avoid the selection of FAK target sequences similar to known non-FAK genes.

The FAK antisense oligonucleosides of the present invention may be of any suitable length, but preferably are between about 6 to about 40 nucleosides in length, and more preferably between about 12 to about 30 nucleosides. The length of a particular antisense compound, the number of complementary bases in the compound, and the identity and location of the complementary bases may be adapted so that suitable target specificity and binding affinity will be achieved under the conditions in which the compound will be used. These conditions include, for example, the effective concentration of the antisense compound inside the cell, the concentration and turnover rate of the target sequence, the desired level of reduction of concentration of the target sequence, the efficacy of expression inhibition, and the mode of inhibition (e.g., catalytic or non-catalytic).

The present FAK antisense compounds preferably are modified to render them resistant to degradation by cellular nucleases or other enzymes that are present in vivo. This modification can be accomplished by methods known in the art, e.g., by incorporating one or more internal artificial internucleoside linkages (such as by modifying the phosphodiester linkage to include alternate or additional groups in conjunction with a phosphorus atom, e.g., by replacing one of the non-bridging phosphate oxygens in the linkage with sulfur, methyl or other atoms or groups), and/or by blocking the 3' end of the oligonucleoside with a capping structure. Preferred examples of such nuclease-resistant non-phosphodiester linkages include phosphorothioate, phosphorodithioate, alkyl- (especially methyl-) and arylphosphonate, phosphoramidate, phosphotriester, alkyl- (especially methyl-) and arylphosphonothioate, aminoalkyiphosphonate, aminoalkylphosphonothioate, phosphorofluoridate, boranophosphate, silyl, formacetal, thioformacetal, morpholino and peptide-based linkages. Mixtures of such linkages, including mixtures with one or more phosphodiester linkages, are likewise useful and can be utilized to adjust the binding affinity, specificity and expression inhibition characteristics of the subject compounds while maintaining a suitable level of nuclease resistance.

Synthetic methodologies for preparing antisense compounds containing such backbone linkages are known in the art. For example, commercial machines, reagents and protocols are available for the synthesis of oligonucleosides having phosphodiester and certain other phosphorus-containing internucleoside linkages. See, for example, Gait, M. J., *Oligonucleotide Synthesis: A Practical Approach* (IRL Press, 1984); Cohen, Jack S., *Oligodeoxynucleotides Anti-sense Inhibitors of Gene Expression* (CRC Press, Boca Raton Fla., 1989); and *Oligonucleotides and Analogues: A Practical Approach* (F. Eckstein, 1991); Agrawal, S. (ed.), *Protocols for Oligonucleosides and Analogs Methods in Molecular Biology*, Vol. 20 (Humana Press, Totowa N.J. 1993). Synthetic methods for preparing methylphosphonate oligonucleosides are described in Agrawal, above, Chapter 7, pages 143–164 (Hogrefe, R. I.), and in PCT Application Nos. WO 92/07864 and WO 92/07882. Preparation of oligonucleosides having various non-phosphorus-containing internucleoside linkages (such as morpholino, formacetal and peptide nucleic acid (PNA) linkages and the like) is described in, for example, U.S. Pat. No. 5,142,047 and in PCT Publication Nos. WO 92/02532 (Reynolds, M. A., et al.) and WO 93/13121 (Cook, P. D.). The disclosures of these synthetic methodology references are incorporated herein by reference.

Where it is desired to use an antisense compound that is capable of activating RNase H for cleavage of the target FAK nucleic acid, a number of other structural considerations come into play. First, it has been reported that uncharged backbone linkages are incapable of activating RNase H. As a result, such antisense compounds should include an RNase H activating portion comprising at least about three consecutive charged (anionic) internucleoside linkages, as for example phosphodiester, phosphorothioate or phosphorodithioate linkages or mixtures thereof. Second, it has been reported that various 2'-sugar substituents (particularly electron-withdrawing groups such as 2'-O-alkyl or 2'-fluoro) will render the substituted portion of the antisense strand non-activating to RNase H, even though binding affinity toward the target nucleic acid is increased. Inoue, H., et al., FEBS Letters 215:327–330 (1987); Monia, B. P., et al., J. Biol. Chem. 268:14514–522 (1993). Accordingly, the charged-backbone RNase H activating portion of such compounds should be 2'-unsubstituted, although 2'-substituents may usefully be employed in other (particularly terminal) non-activating portions of the compound to increase binding affinity. Third, in order to increase nuclease resistance in such antisense compounds, it is preferred to incorporate non-phosphodiester backbone linkages, as for example methylphosphonate, phosphorothioate or phosphorodithioate linkages or mixtures thereof, into one or more non-RNase H-activating regions of the compounds. Such non-activating regions may additionally include 2'-substituents as discussed above, and, as discussed below, may include chirally-selected backbone linkages in order to increase binding affinity and duplex stability.

Other functional groups may also be joined to the oligonucleoside sequence to instill a variety of desirable properties, such as to enhance uptake of the oligonucleoside sequence through cellular membranes, to enhance stability or to enhance the formation of hybrids with the target nucleic acid, or to promote cross-linking with the target (as with a psoralen photo-cross-linking substituent). See, for example, PCT Publication No. WO 92/02532. Examples of cellular-uptake or membrane-disruption moieties include polyamines, e.g. spermidine or spermine groups, or polylysines; lipids and lipophilic groups; polymyxin or polymyxin-derived peptides; octapeptin; membrane pore-forming peptides; ionophores; protamnine; aminoglycosides; polyenes; and the like. Other potentially useful functional groups include intercalating agents; radical generators; alkylating agents; detectable labels; chelators; or the like.

Where it is desired to effect cleavage of the target FAK nucleic acid strand with the antisense compound, a suitable cleavage moiety may be incorporated into the compound. Such cleavage moieties preferably include functional groups selected to achieve one or more of the functions associated with enzymatic cleavage of RNA. These functions include (1) providing a nucleophilic moiety for attack on the target phosphorus atom, especially by deprotonation of the 2'-OH hydrogen of a target sugar in the target region of the FAK RNA (as achieved, for example, by increasing the local pH about the target sugar and/or by providing a basic or nucleophilic moiety in the vicinity of the target sugar); (2) supplying a proton or other electrophilic moiety for interaction with a phosphorus-bonded lone oxygen atom of the target RNA to form, for example, a protonated phosphate diester (as achieved, for example, by operation of an acidic or electrophilic moiety of the cleavage compound); (3) stabilizing the cleavage transition state, i.e., providing a structure on the cleavage compound to stabilize the intermediate structure or structures assumed by the target RNA during the cleavage mechanism, as by the inclusion of an acid-base moiety and/or other moieties which afford charge neutralization or hydrogen bonding stabilization to the intermediate (particularly polyfunctional groups capable of stabilizing a dianionic phosphorane in a trigonal bipyramidal configuration); and (4) providing a structure to protonate the leaving 5'-O oxygen atom of the target site, as by operation of an acidic moiety of the cleavage compound. See generally Jubian, et al., J. Am. Chem. Soc. 114:1120-1121 (1992), which is incorporated by reference. Preferably, the cleavage moiety comprises two or more distinct functional groups selected to provide two or more of the functions of proton donation, proton acceptance, hydrogen bonding and charge neutralization. Among these are cleavage moieties comprising two or more amino groups, and wherein at least one amino group is substantially protonated, and at least one amino group is substantially nonprotonated, at physiological pH. Additionally, or alternatively, the cleavage compounds may include a strong Lewis acid moiety, as for example a chelated metal species, which activates the phosphorus-oxygen center of a target phosphodiester bond (or of a target pyrophosphate linkage in the case of a 5'-cap region of a target RNA sequence) for direct hydrolytic cleavage by in situ water or hydroxide ion. In addition, such antisense cleavage compounds will preferably include a substituent or portion that facilitates rotation of a target RNA sugar portion about the phosphodiester backbone of the target RNA, preferably to position a 2'-OH group of the target RNA for in-line, intramolecular attack on a neighboring phosphorus atom of the target backbone (as achieved, for example, by incorporating an intercalating moiety, a base-omission mismatch, or some other non-complementary structure within the cleavage compound).

Oligonucleosides having one or more chirally pure internucleosidyl linkages (particularly Rp-chiral linkages) may be used and may be preferred in order to increase binding affinity between the subject antisense compounds and the target FAK nucleic acid sequence. Such oligonucleosides, for example with methylphosphonate or phosphorothioate linkages, may be prepared using methods as those described in Lesnikowski, et al., Nucleic Acids Research 18(8) :2109–2115 (1990), Stec, et al., Nucleic Acids Research 19(21):5883–5888 (1991), Cook, U.S. Pat. No. 5,212,295, or PCT Publication No. WO 93/08296 (Hoke, G. D. & Cook, P. D.). These references are likewise incorporated by reference herein.

The FAK antisense compounds for use in the instant invention may be administered singly, or tandem or separate combinations of the compounds may be administered for adjacent or non-neighboring targets or for combined effects of anti-sense mechanisms in accordance with the foregoing general mechanisms. For example, two separate tandem antisense compounds having complementarity to neighboring target subregions in the FAK nucleic acid strand may be used, where one of the tandem compounds provides a cleavage moiety and the other tandem compound provides a non-complementary structure as described above. Alternatively, each of the two tandem compounds may provide some portion of an RNase H activating region, or some portion of a cleavage moiety, whereby the two compounds act cooperatively following hybridization to adjacent regions in the target strand to effect cleavage or other inhibition of expression of the target strand. Such tandem compounds would be expected to provide greater target specificity (and decreased inhibition of unintended nucleic acid sequences) inasmuch as separate hybridization of two separate antisense compounds is required to achieve inhibition.

B. Methods and Therapeutic Compositions

When used in mammalian therapy, the FAK antisense compounds may be administered in any convenient vehicle that is physiologically acceptable. The compounds can be formulated for a variety of modes of administration, including systemic, topical or localized administration. Techniques and formulations generally may be found in *Remington's Pharmaceutical Sciences*, Mack Publishing Co., Easton, Pa., latest edition. In each case, a therapeutically effective amount of the antisense compound is administered in order to prevent or inhibit the translation of the target FAK nucleic acid. The antisense compound is generally combined with a carrier such as a diluent or excipient which may include fillers, extenders, binding, wetting agents, disintegrants, surface-active agents, or lubricants, depending on the nature of the mode of administration and dosage forms. Typical dosage forms include tablets, powders, liquid preparations including suspensions, emulsions and solutions, granules, capsules and suppositories, as well as liquid preparations for injections.

In the pharmaceutical formulation the antisense compound may be contained within a lipid particle or vesicle, such as a liposome or microcrystal, which may be suitable for parenteral administration. The particles may be of any suitable structure, such as unilamellar or plurilamellar, so long as the antisense oligonucleotide is contained therein. Positively charged lipids such as N-[1-(2,3-dioleoyloxi) propyl]-N,N,N-trimethyl-amoniummethylsulfate, or "DOTAP," are particularly preferred for such particles and vesicles. The preparation of such lipid particles is well known. See, e.g., U.S. Pat. Nos. 4,880,635 to Janoff et al.; 4,906,477 to Kurono et al.; 4,911,928 to Wallach; 4,917,951 to Wallach; 4,920,016 to Allen et al.; and 4,921,757 to Wheatley et al. Other non-toxic lipid based vehicle components may likewise be utilized to facilitate uptake of the antisense compound by the cell.

For systemic administration, injection may be preferred, including intraarterial, intravenous and intraperitoneal injection (which are especially preferred), as well as intramuscular and subcutaneous injection. For injection, the cleavage compounds of the invention are formulated in liquid solutions, preferably in physiologically compatible buffers such as Hank's solution or Ringer's solution. In addition, the compounds may be formulated in solid form and redissolved or suspended immediately prior to use. Lyophilized forms are also included. In some instances, the compositions may be infused upstream from the site of the cells whose activity is to be modulated. Implantable drug pumps, as for example Infusaid® pumps (Infusaid, Inc.), are useful for delayed-release intraarterial administration.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucosal administration. In addition, detergents may be used to facilitate permeation. Transmucosal administration may be through use of nasal sprays, for example, as well as formulations suitable for administration by inhalation, or suppositories. For oral administration, the oligonucleosides are formulated into conventional as well as delayed release oral administration forms such as capsules, tablets, and tonics.

Antisense compounds of the invention may also be administered by introducing into the cell a DNA construct which produces an antisense compound as described herein within the cells. Such a DNA construct typically contains, in operable association with one another, a transcriptional promoter segment operable in the target cell, a DNA segment that encodes the antisense compound, and a transcription termination segment. Such DNA constructs may be provided in a pharmaceutical formulation as described herein. Such DNA constructs are made and used in accordance with known techniques as set forth in M. Inouye, U.S. Pat. No. 5,190,931, the disclosure of which is incorporated by reference herein in its entirety.

For topical administration, the oligonucleosides for use in the invention are formulated into ointments, salves, gels, or creams, as is generally known in the art.

The localized concentration or amount administered to an animal subject may be determined empirically and will depend upon the purpose of the administration, the area to be treated, the effectiveness of the composition, and the manner of administration. The localized concentration at the site of the targeted cells will desirably be in the range of about 0.05 to 50 $\mu$M, or more particularly 0.2 to 5 $\mu$M, although higher or lower dosages may be employed as appropriate. In particular, it is contemplated that relatively high dosage levels may safely be employed in the present context because the FAK gene is overexpressed in cancer cells, and is expressed at relatively low levels in non-cancerous cells. For administration to a subject such as a human, a dosage of from about 0.01, 0.1, or 1 mg/kg up to 50, 100, or 150 mg/kg or more may typically be employed.

The present compounds may also be used in in vitro, ex vivo or in other non-therapeutic modes in order to study the biological properties of the FAK gene and protein, and their role in normal or cancer cell development, propagation, migration and the like. The present invention is also useful in vitro in tissue culture and fermentation techniques where it is desired to inhibit or reduce cell adhesion to facilitate growth of the cells, subsequent processing of the cells, production of proteins or other compounds from the cells, etc. Other uses of the present invention, and suitable antisense compounds to achieve the goals of the invention, will be apparent to those skilled in the art in view of the present disclosure, including the examples that follow. However, it will be understood that the specific examples herein, and the specific antisense structures described, while useful in appreciating the utility of the invention, are not intended to limit the scope of the invention as claimed hereinafter.

C. EXAMPLES

Example 1

Preliminary Studies—Isolation of Human FAK Homolog and Measurements of Cellular Expression In preliminary studies relating to the present invention, homologous tyrosine kinase gene fragments were cloned from human cell lines and primary human tumors using low stringency PCR amplification and degenerate oligonucleotide primers based on catalytic domain consensus sequences common to all tyrosine kinases. Cance, W. G., et al., Int. J. Cancer 54:571–577 (1993) (incorporated by reference herein). Using these methods, a 210 bp gene fragment of the human homolog of FAK was isolated from a primary human sarcoma, and was found to be expressed in sarcoma, breast and colon cell lines. Weiner, T. M., et al., Ann. Surg. Oncol. 1:18–27 (1994) (incorporated by reference herein). The expression of FAK in normal, adenomatous, invasive, and metastatic human tissue was also studied. Using Northern analysis, increased levels of FAK were found in 1 of 8 adenomatous tissues, in 17 of 20 invasive tumors, and in all 15 metastatic tumors. Paired samples of normal tissue did not express detectable FAK mRNA. See Table 1. This association of FAK overexpression with invasion and metastasis was a finding common to both the epithelial and mesenchymal tumors analyzed. Furthermore, upon comparison of the levels of FAK mRNA in paired samples from colon cancer patients, a progressive increase in densitometrically indexed FAK mRNA was found in 3 of 4 samples as the tumor invaded and metastasized. Weiner, T. W., et al., The Lancet 342:1024–1025 (1993) (incorporated by reference herein). These studies are believed to have established the first translational link of FAK expression to the progression of human cancer.

TABLE 1

SUMMARY OF NORTHERN ANALYSES OF FAK IN HUMAN TUMORS

| TISSUE: | NORMAL | BENIGN | PRIMARY | METASTASIS |
|---|---|---|---|---|
| Colon | 0/4 | 1/6 | 7/8 | 7/7 |
| Breast |  | 0/2 | 9/11 | 4/4 |
| Other* | 0/2 |  | 1/1 | 4/4 |
| Total | 0/6(0%) | 1/8(12%) | 17/20(85%) | 15/15(100%) |

*Normal muscle (2), Primary Thyroid Carcinoma (1) with paired nodal metastasis (1), Metastatic Carcinoid (1), Squamous Cell Carcinoma (1) and Melanoma (1)

Example 2

Identification and Characterization of a Human FAK cDNA Clone

The 210 bp FAK gene fragment described above was used as a probe to isolate larger cDNA clones. A cDNA library was first constructed from the BT-20 human breast cancer cell line. Poly-A+ RNA was isolated from BT20 cells, and first strand synthesis was carried out using a poly-T primer and Maloney-Murine Leukemia Virus Reverse Transcriptase. Synthesis of the second strand was performed using DNA Polymerase I, followed by ligation of Not1 linker adapters, Not1 restriction endonuclease digestion, and ligation of the cDNA fragments into a Not1 digested cloning vector. A cDNA clone, spanning 1052 amino acids of the predicted sequence, was identified (see FIG. 1, "HUMFAK").

The clone was found to be homologous to both the mouse and chicken FAK sequences and identical to a recently-published human cDNA clone derived from T-cells (Whitney, G. S., et al., DNA Cell Biology 12:823–830 (1993)).

Example 3

Generation of Recombinant FAK Polypeptide and Anti-FAK Polyclonal Antibodies

A 198 bp segment of the FAK cDNA clone of the preceding example was subcloned into a pQE expression vector as described in Bujard, H., et al., Methods in Enzymology 155:416–433 (1987). Fusion protein expression was induced by IPTG at 37° C., followed by purification under denaturing conditions on a Ni-NTA resin column. This provided a hexahistidine fusion protein containing an amino-terminal 6 kD fragment of the FAK clone. This segment of the FAK protein (see FIG. 1) was selected in order to allow generation of FAK-specific polyclonal antibodies which would not cross-react with the carboxy-terminal 41 kD) FAK-related non-kinase protein (FRNK, see Schaller, M. D., et al., Mol. Cell. Biol. 13:789–791 (1993)). The purified fusion protein was analyzed by SDS/PAGE, excised from the gel and injected into rabbits to prepare polyvalent sera.

The antisera recognized a 125 kD protein by Western blotting against cell lines (C8161, RD, BT20) known to overexpress FAK. The rhabdomyosarcoma (RD) cell line was grown in RPMI-1640 with 10% heat-inactivated fetal calf serum (FCS), penicillin (100 units/ml) and streptomycin (100 mg/ml). The C8161 and BT20 cell lines were likewise grown in RPMI-1640, and maintained at 37° C. in a 5% $CO_2$ incubator. Antibody characterization further included titering studies to a 1/5000 dilution along with blocking experiments. Antibody reactivity was completely inhibited by the addition of recombinant 6 kD blocking peptide. Blocking was accomplished by preincubation of the titered antisera with progressive levels of the recombinant antigenic peptide prior to Western analysis until complete attenuation of the 125 kD signal.

Example 4

Protein-level Measurement of FAK Overexpression in Normal and Cancerous Tissue and Cell Lines The expression of $p125^{FAK}$ was measured in a variety of normal and cancerous human tissue and cell line samples using the anti-FAK antibody obtained as described above.

Initially, FAK expression in the RD (embryonal rhabdomyosarcoma), BT20 (breast adenocarcinoma), HT29 (colon adenocarcinoma), C8161 (melanoma) and other human tumor cell lines was studied. As shown in FIG. 2, the highest levels of expression occurred in the RD cell line, but expression was also detected in the BT20, HT29 and C8161 lines. In contrast, some of the cell lines (such as the breast cell line SK-BR-3) expressed low levels of $p125^{FAK}$.

The anti-FAK antibody was also used to assess the change in levels of $p125^{FAK}$ expression in normal, neoplastic, invasive and metaplastic human tissues. In particular, 91 different tissue samples including epithelially-derived colon and breast cancers, as well as mesodermally-derived sarcomas were studied by Western blot analysis. Colon samples included normal mucosa only; benign, non-invasive polyps; invasive polyps; invasive primary cancers and both liver and peritoneal metastatic specimens. Breast samples included benign, non-invasive fibroadenomas; normal breast tissue paired with the infiltrating ductal lesions and a lymph node metastasis. Sarcoma samples included normal muscle; benign mesenchymal tumors such as lipomas and leiomyomas; invasive sarcomas including leiomyosarcoma, rhabdomyosarcoma, neurofibrosarcoma, liposarcoma, synovial sarcoma and fibrohistiosarcoma. Other specimens studied included normal liver and hypercellular parathyroid lesions.

Figure 3:
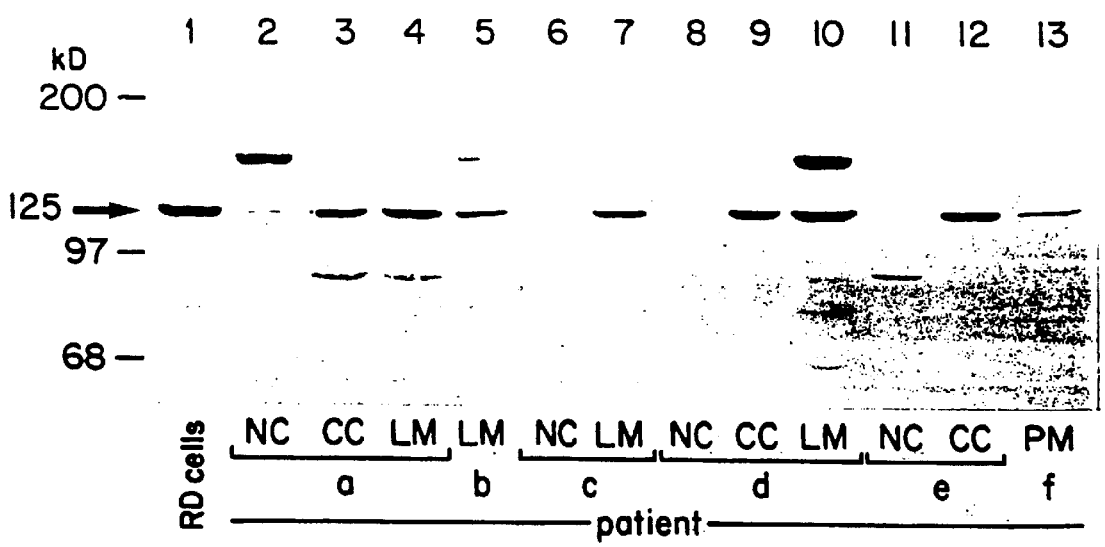
FIG. 3 is a Western blot analysis showing progressive $p125^{FAK}$ expression in 23 paired colorectal tumors as the tumors invade and metastasize, wherein paired samples from individual patients are indicated by letters at the bottom.

By way of example, colon tumor samples were obtained through operative specimens via IRB-approved protocols and banked at the Tissue Procurement Facility of the Lineberger Comprehensive Cancer Center. Protein was extracted from snap-frozen primary tissues. A 1 $cm^3$ section of tissue was placed in 3 ml of NP-40 lysis buffer (1% Triton X-100, 20 mM Tris, pH 7.4, 150 mM NaCl, 5 mM EDTA, 1 mM $Na_3VO_4$, 10 mg/ml each of aprotinin and leupeptin). The tissue was homogenized in the lysis buffer using a Polytron (Brinkman), then centrifuged for 15 minutes at 4° C. in a microcentrifuge. The amount of protein was measured by the BCA protein assay (Pierce, Rockford, Ill.). Cell lysate containing 30 μg of protein was subjected to 10% SDS/PAGE and electroblotted onto a nitrocellulose membrane as described by Towbin, H., et al., Proc. Natl. Acad. Sci. USA 76:4350–4354 (1979). Immunodetection of blotted $p125^{FAK}$ was accomplished using a 1/2000 titer of anti-FAK antibody along with a 1/5000 titer of anti-rabbit IgG horseradish peroxidase conjugate (Amersham) in non-fat milk. The blots were washed several times in 0.1% TBST (20 mM Tris pH 7.4, 150 mM NaCl, 0.1% Tween20) and visualization was achieved by chemiluminescence using the ECL detection system (Amersham) followed by X-ray film exposure. In FIG. 3, which shows Western blots for paired colon cancer series, the labels read as follows: NC, normal mucosa; CC, primary invasive tumor; LM, liver metastasis; PM, peritoneal metastasis; RD, embryonal rhabdomyosarcoma cell line (positive control).

These studies demonstrated the existence of progressive up-regulation of FAK from normal to invasive and metastatic phenotypes, consistent with the transcriptional data described above. The results from the 91 tissue samples are summarized in Table 2. In paired normal and neoplastic colon samples there was no FAK expression in 9 normal mucosal specimens compared to overexpression in 6/7 primary invasive tumors and 9/11 metastatic lesions. These results demonstrated progressive increases in p125$^{FAK}$ expression as tumors invade and metastasize. Additionally, five neoplastic, pre-invasive villous adenomas showed high FAK levels, whereas there was no signal in tubular polyp specimens, suggesting FAK overexpression may be an early event as transformed cells become invasive. In a similar measurements of paired breast cancer samples, 9/16 infiltrating ductal lesions demonstrated FAK overexpression with no signal detectable in the matched normal tissue. Finally, analysis of sarcomas, a histologically diverse family of mesenchymal tumors, showed the highest levels of FAK expression in the biologically aggressive, large (>5 cm), high grade lesions. In contrast to invasive tumors, hypercellular neoplastic tissues without invasive potential, such as parathyroid adenomas, did not overexpress FAK. Significant levels of p125$^{FAK}$ expression were detected in 3 samples of large, colorectal villous adenomas, perhaps indicating that these tumors were in the process of becoming invasive. It was notable that the only tumor which did not express high levels of p125$^{FAK}$ was a retroperitoneal colorectal cancer recurrence which slowly developed and was resected 4 years after initial colectomy. Thus, these results confirmed our initial observations, linking overexpression of FAK to the invasive and metastatic phenotype, and suggested that more rapidly growing tumors expressed higher levels of p125$^{FAK}$.

These observations not only demonstrated up-regulation of p125$^{FAK}$ expression as a tumor became invasive and metastatic, but also suggested that p125$^{FAK}$ overexpression accompanied signaling pathways toward invasion and metastasis for a variety of tumors of both epithelial and mesenchymal origin.

TABLE 2

FAK EXPRESSION IN HUMAN TUMORS

| TISSUE: | NORMAL | NEOPLASTIC NON-INVASIVE | PRIMARY INVASIVE | METASTASIS |
|---|---|---|---|---|
| Colon | 0/9 | 5*/6 | 6/7 | 9/11 |
| Breast | 0/16 | 0/2 | 9/16 | 1/1 |
| Sarcoma | 0/2 | 0/5 | 8/8 | 2/2 |
| Other** | 0/2 | 0/4 | — | — |
| Total | 0/29 | 5/17 | 23/31 | 12/14 |

*Villous adenomas (>2 cm)
**Normal liver (2), Parathyroid adenoma (4)

Example 5
Effect of Antisense Oligonucleosides in Inhibiting FAK Expression and FAK-Related Biological Activities Antisense oligodeoxyribonucleotides having complementarity to portions of the human FAK mRNA were synthesized in order to study their efficacy in inhibiting FAK expression in human tumor cells and their effect on the FAK-related biological properties of the cells. It was shown that the antisense compounds were not only useful in inhibiting FAK expression, but also inhibited tumor cell growth, cellular adhesion properties, cell motility, cell colony formation, and tumor formation. The compounds were also found to induce cell apoptosis.

A. Synthesis of Oligodeoaribonucleosides

Two separate regions near the 5'-terminus of the human FAK clone were selected for targeting by antisense oligodeoxyribonucleotides (see FIG. 1). Complementary phosphorothioate-linked antisense oligonucleosides having, respectively, 20 and 24 nucleosides were prepared with the following sequences:

FAK1AS: 5'-ACACTTGAAGCATTCCTTATCAAA-3' (SEQ ID NO:4)

FAK2AS: 5'-ATAATCCAGCTTGAACCAAG-3' (SEQ ID NO:5)

These sequences have complementarity with the selected target regions of the human FAK mRNA as follows:

```
HUMFAK    ...Phe Asp Lys Glu Cys Phe Lys Cys ...    (SEQ ID NO:12)

5'-...UUU GAU AAG GAA UCG UUC AAG UGU ...-3'  (SEQ ID NO:9)

FAK1AS    3'-AAA CTA TTC CTT AGC AAG TTC ACA -5'    (SEQ ID NO:4)

HUMFAK    ...Leu Gly Ser Ser Trp Ile Ile ...         (SEQ ID NO:13)

5'-...CUU GGU UCA AGC UCG AUU AUU ...-3'      (SEQ ID NO:11)

FAK2AS    3'-GAA CCA AGT TCG ACC TAA TA-5'           (SEQ ID NO:4)
```

In addition, control sequences having a 2-base or a 5-base mismatches were prepared as follows (mismatched bases are underlined):

MSN1: 5'-ATAATCGAGCTTCAACCAAG-3' (SEQ ID NO:6)

MSN2: 5'-ATAATCGACGTTCAAGCAAG-3' (SEQ ID NO:7)

An additional "nonsense" control sequence, derived from the mouse wnt protooncogene which was not expressed in the cell lines under study, was also prepared for use in certain of the studies described below:

WNT: 5'-AGCCCGAGCAGGTGGGGCTC-3' (SEQ ID NO:8)

The specificity of these sequences was confirmed in GeneBank.

The oligonucleosides were synthesized using standard phosphoramidite chemistry, in the course of which the internucleoside linkages were converted to phosphorothioate linkages to prevent cellular degradation by RNases. After synthesis, the oligonucleosides were extracted several times with phenol-chloroform, and then ethanol-precipitated and reconstituted in Hanks' balanced salt solution (HBSS) and frozen at −20° C. for storage.

B. General Procedures for Application of Antisense Oligonucleosides to Cell Samples In the following studies, the oligonucleosides were first preincubated to a final concentration of 0.15 μM with 0.3% lipofection reagent (Gibco BRL) in serum-free Opti-Mem medium (Gibco BRL) in order to form a stable lipid-DNA complex for optimizing transfection. Cell samples were typically prepared by seeding approximately $2 \times 10^5$ cells in six-well tissue culture plates with 2 ml of medium, and incubating to 60% confluence. As detailed below, the cells studied included melanoma (C8161), embryonal rhabdomyosarcoma (RD) and breast adenocarcinoma (BT20) cells. The growth medium typically comprised 2 ml RPMI-1640 with 10% heat-inactivated fetal calf serum (FCS), penicillin (100 units/ml) and streptomycin (100 $\mu$g/ml). Normal human fibroblast (NHF) cell lines were grown in Eagle's MEM supplemented with 10% FCS.

The lipid-DNA solution was applied to the cells under study by gently overlaying a measured portion of the solution onto a 60% confluent monolayer of cells, followed by incubation for a measured time (typically 0–24 hours) at 37° C. in a 5% $CO_2$ incubator. After this time, the antisense oligonucleoside containing medium was typically removed and the suspension cells isolated, washed and resuspended into 2 ml of normal growth medium. As appropriate, the resuspended cells were replaced onto the remaining adherent cell population for further study.

C. Inhibition of p125$^{FAK}$ Expression by FAK Antisense Compounds

Equal numbers of cells were cultured in six-well tissue culture plates and exposed to oligonucleoside/lipofectin reagent solution for varying periods (0–24 hours) as described above. The cells were then allowed to recover for 24 hours. Measurement of p125$^{FAK}$ expression was performed by Western blot analysis with the FAK-specific antibody described above following standard protein level analysis (Pierce).

Figure 4:
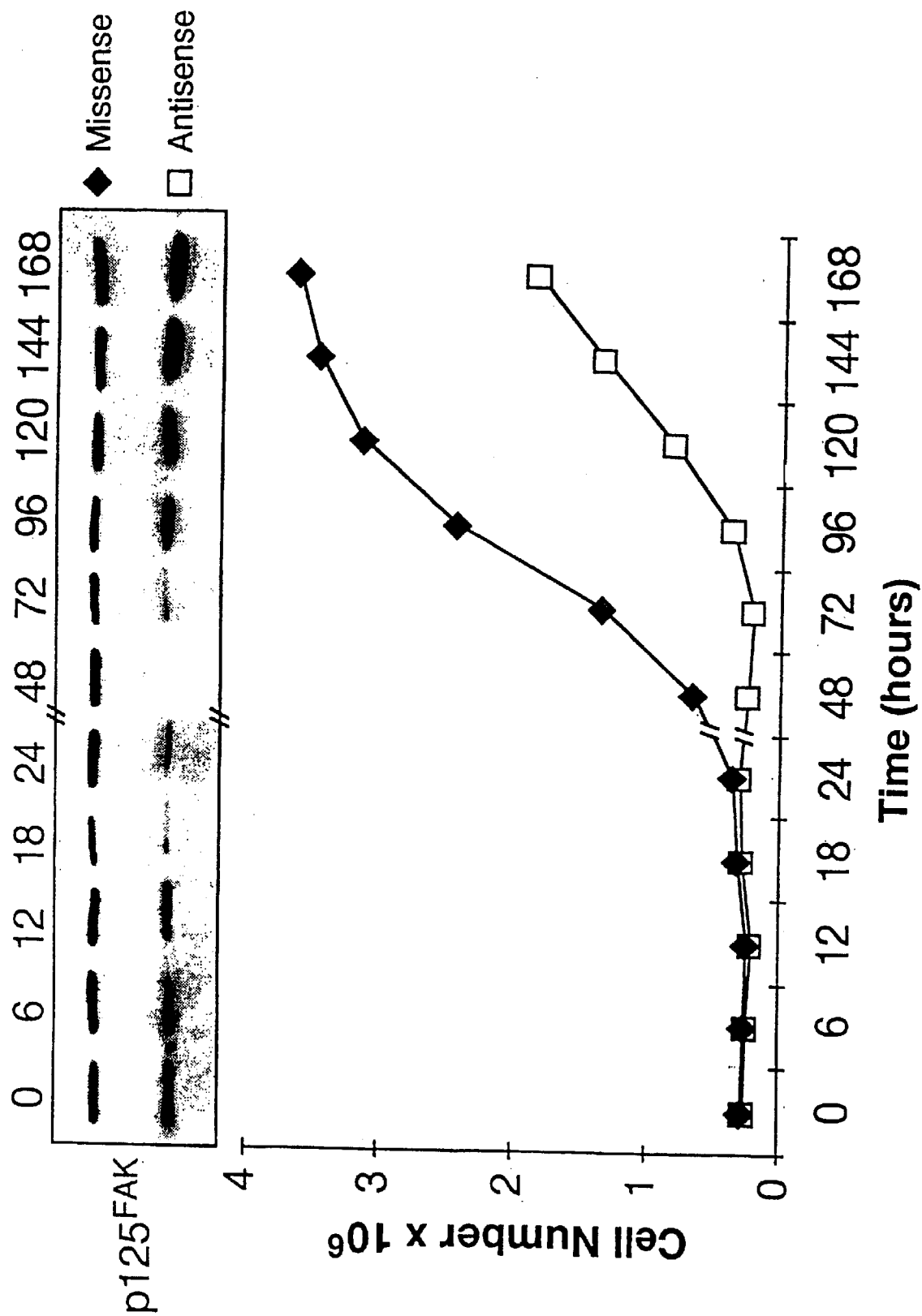
FIG. 4 is a Western blot analysis (top) and a graph (bottom) showing the time course of $p125^{FAK}$ expression in C8161 cells exposed to an FAK antisense compound of the invention and to a missense control.

Attenuation of p125$^{FAK}$ expression in C8161 cells began after 12 hours of exposure to antisense compounds FAK1AS (SEQ ID NO:4) and FAK2AS (SEQ ID NO:5) and was completely abrogated by 18 hours, as exemplified in FIG. 4. Under the same conditions, no significant reduction in p125$^{FAK}$ expression occurred in cells treated with the 5-base mismatch sequence MSN2 (SEQ ID NO:7) or with lipofectin alone. There was a significant attenuation of p125$^{FAK}$ expression with the 2-base mismatch sequence MSN1 (SEQ ID NO:6), although not as complete as with the antisense sequences. FAK expression was seen to recover by 4 days after antisense treatment.

Figure 5:
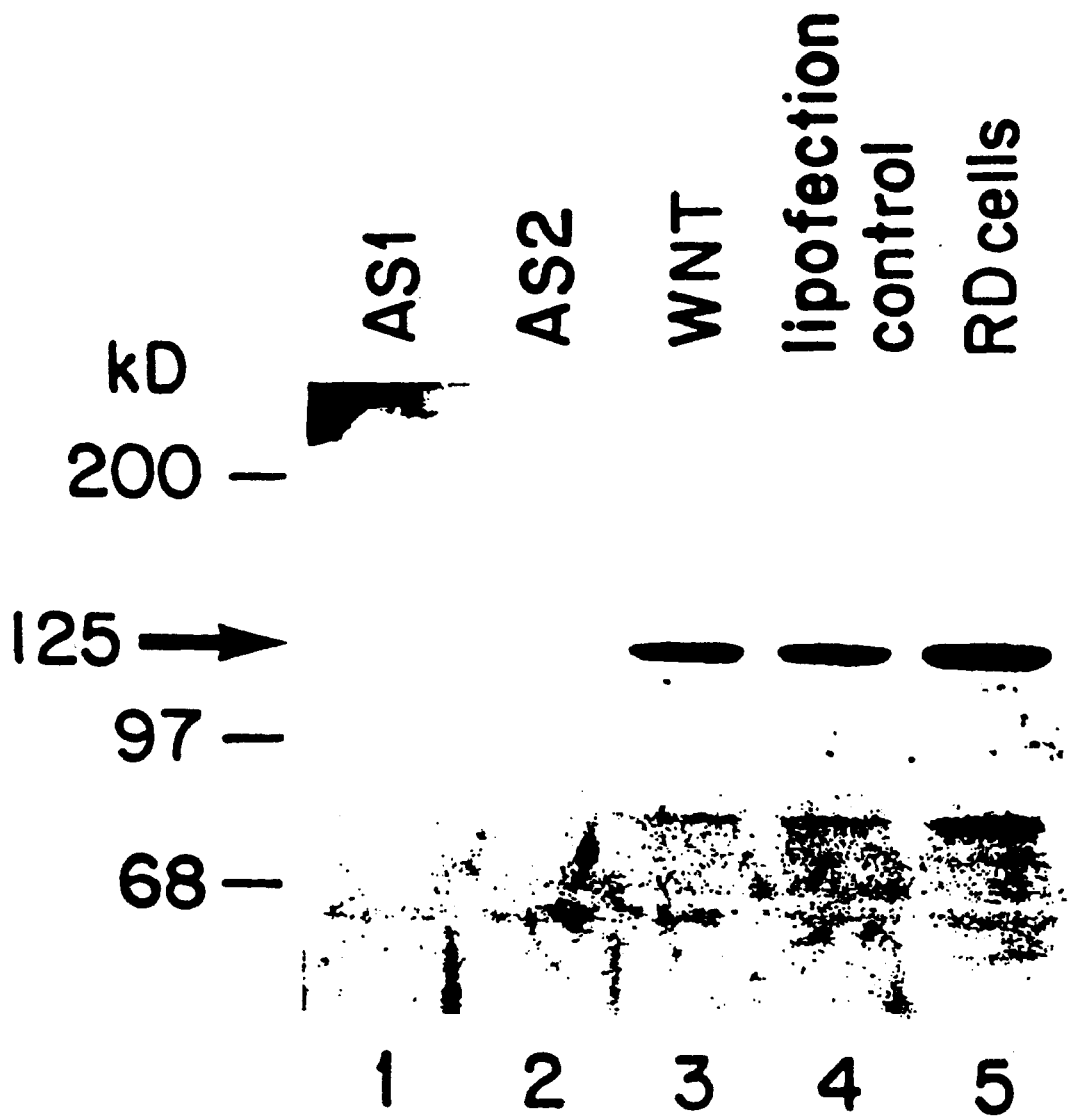
FIG. 5 is a Western blot analysis showing specific attenuation of $p125^{FAK}$ expression in RD cells treated with FAK antisense compounds FAK1AS (SEQ ID NO:4) (lane 1) and FAK2AS (SEQ ID NO:5) (lane 2), as well as control samples treated with an equivalent concentration of nonsense compound WNT (SEQ ID NO:8) (lane 3) or with 0.3% lipofectin (lane 4), and untreated control cells (lane 5).

Similar attenuation of FAK expression was obtained when RD cells were treated with the antisense compounds. As shown in FIG. 5, both antisense oligonucleosides completely abrogated p125$^{FAK}$ expression, whereas there was only a minimal reduction in FAK expression in the control samples treated with the WNT oligonucleoside (SEQ ID NO:8) or with lipofectin (0.3%) alone. In addition, the total protein concentrations in the RD cells did not change with FAK attenuation, as indicated by simple Coomassie-stained gels of total protein extracts.

The effects of the antisense oligonucleosides appeared to be highly specific for FAK. Since application of certain oligonucleotide sequences is known to result in general inhibition of gene expression, we examined the expression in antisense treated cells of other tyrosine kinases known to associate with FAK. The expression of p60$^{src}$ and p59$^{fyn}$ were not significantly altered in these cells. These results suggested not only that the antisense effects of FAK were specific, but also that FAK may function as a downstream element to src and fyn in these cellular signaling pathways.

Figure 6:
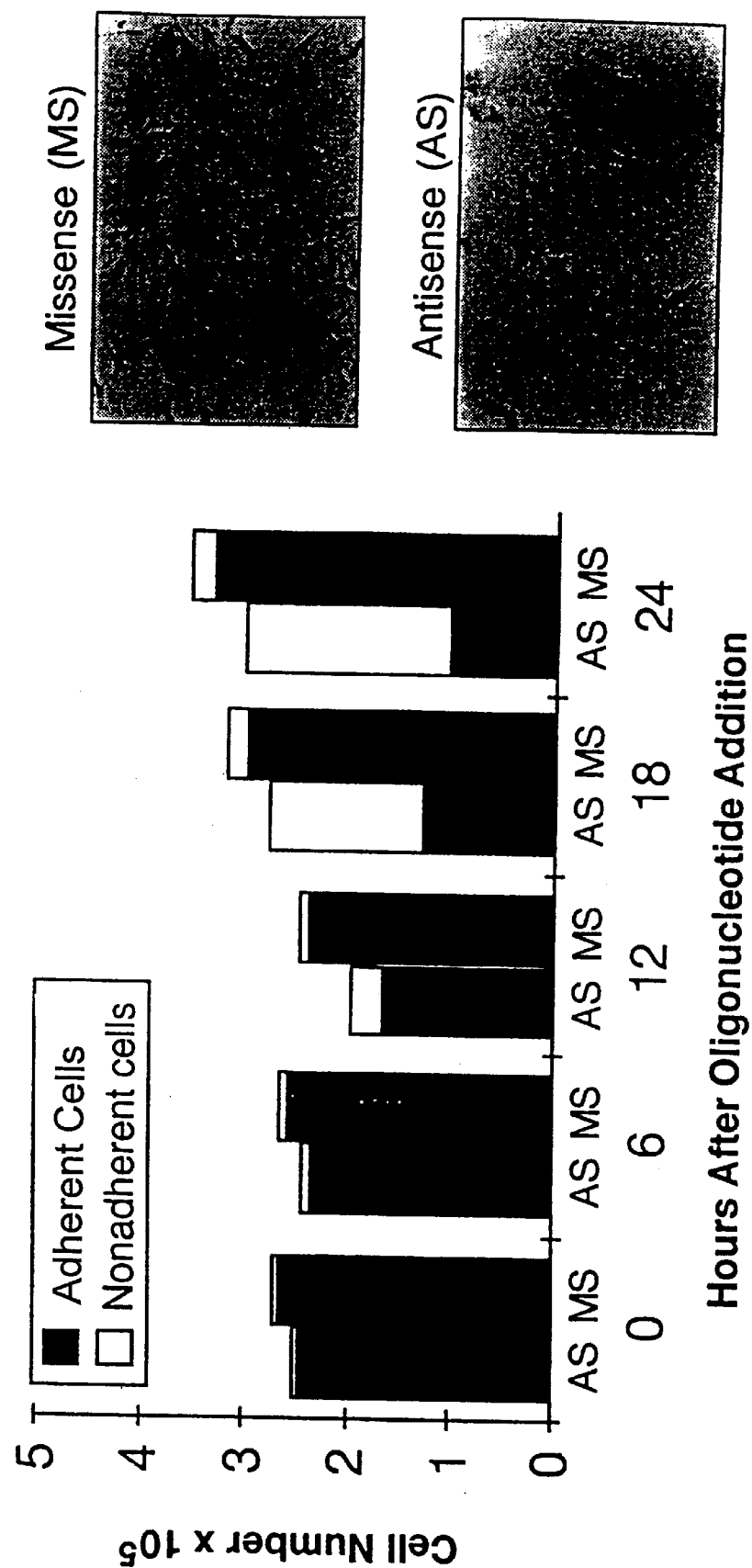
FIG. 6 is a bar graph (left) showing loss of cell adhesion in C8161 cells treated with an FAK antisense compound of the invention as compared to control samples treated with a 5 bp missense compound, and a depiction of stained adherent cells (right) obtained 24 hours after treatment.

D. Inhibition of Cellular Adhesion and Cell Growth by FAK Antisense Compounds Disruption of FAK signalling pathway with the FAK antisense oligonucleosides was shown to cause profound changes in cell phenotype. The most significant change observed was a marked loss of cellular adhesion (see FIG. 6). In each of the model cell lines (C8161, RD and BT2D), the antisense oligonucleosides appeared to disrupt the cell-matrix interactions. After exposure to antisense, treated cells showed a tendency to round-up and enter suspension. This cellular morphologic effect was progressive throughout the duration of antisense oligonucleoside exposure and continued beyond the twenty-four hour treatment period.

By way of example, the effect of the antisense compounds FAK1AS (SEQ ID NO:4) and FAK2AS (SEQ ID NO:5) on cellular adhesion properties was measured by exposing C8161 cells to FAK antisense or to the 5 bp missense control MSN2 (SEQ ID NO:7) for 24 hours. The numbers of cells adherent to the cell culture plates (solid bar) and cells in suspension (white bar) were counted at 0, 6, 12, 18 and 24 hours after antisense or control oligonucleosides were added (see FIG. 6). Loss of adherence in the FAK antisense-treated cells began between 12 and 18 hours after oligonucleoside addition, correlating with the loss of p125$^{FAK}$ expression (FIG. 4). This loss of adhesion was also visualized in hematoxylin and eosin-stained cells 24 hours after FAK antisense treatment. Cells treated with the 5 bp missense sequence MSN2 (SEQ ID NO:7) retained their normal adherent characteristics in the staining studies. Similar inhibition of cell adhesion was observed with RD and BT20 cells treated with FAK antisense oligonucleosides.

Figure 7:
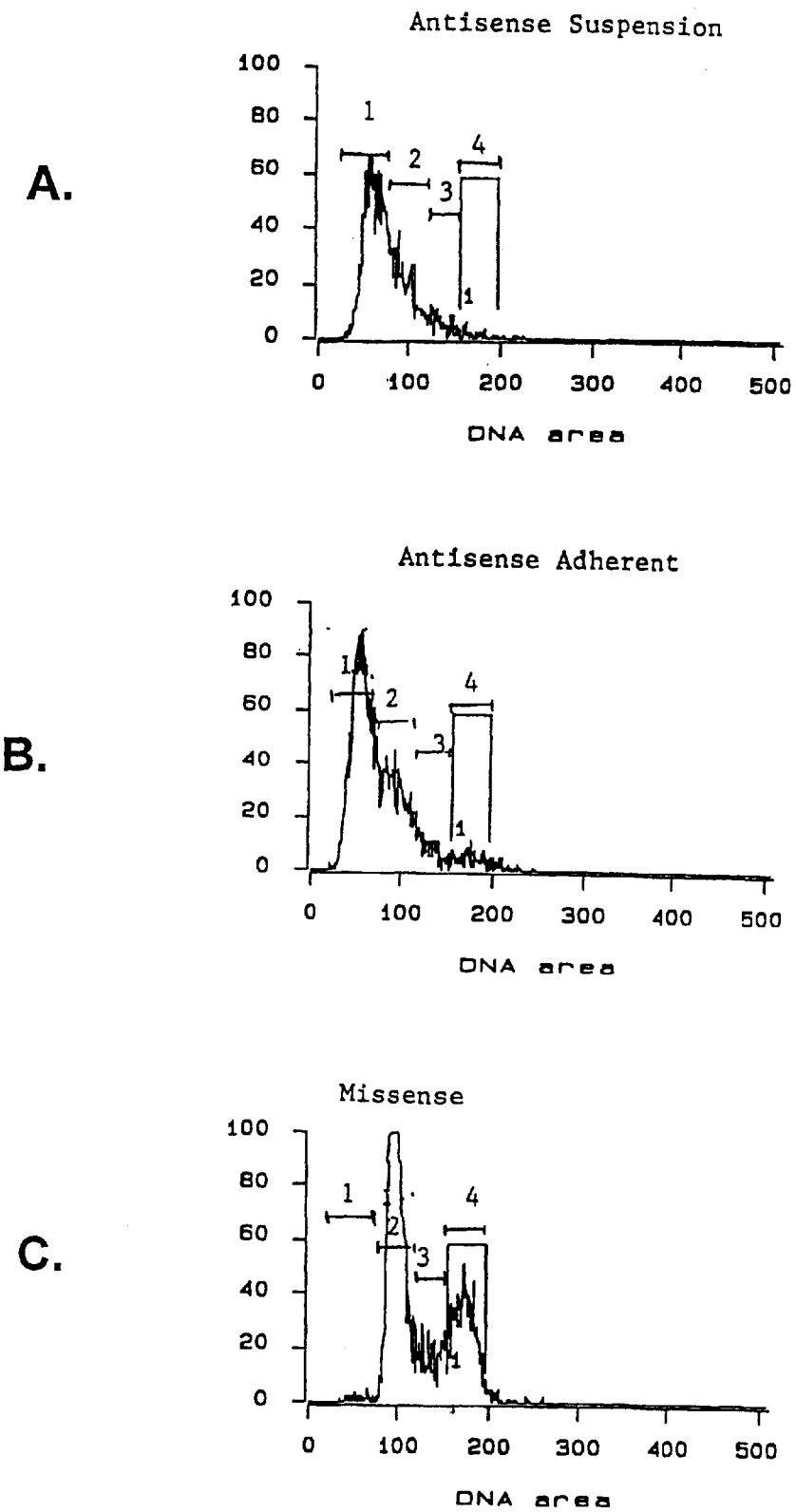
FIGS. 7A-7C are graphs depicting flow-cytometric analyses of C8161 suspension (7A) and adherent (7B) cells treated with an FAK antisense compound of the invention, or with a 5 bp missense compound (7C).

Evaluation of non-adherent antisense-treated cells by trypan blue exclusion showed greater than 90% viability. Flow-cytometric analysis of propidium iodide-stained C8161 suspension cells (20 $\mu$g/ml propidium iodide in PBS cells, fixed in 70% ethanol) indicated that the DNA content of 60% of the non-adherent population was less than 2n. The cells appeared as a gaussian peak to the left of $G_0G_1$ which is characteristic of apoptosis (FIG. 7). Furthermore, the non-adherent cells appeared to be arrested in the G1 phase. These flow cytometric findings correlated with the inhibition on cell growth observed following antisense therapy. Furthermore, the C8161 cells showed no significant growth for three days (72 hours) following exposure to antisense oligonucleosides while MSN2 control treatments showed no alterations in transformed cell growth. The effects on C8161 cells specifically correlated with the antisense attenuation of p125$^{FAK}$ expression (FIG. 4). Similar growth inhibition effects were observed in RD and BT20 cells treated with FAK antisense oligonucleosides. These observations are similar to the anoikis phenomenon described by Frisch, et al. (J. Cell Biology 124:619–626 (1994)) and is a further indication that FAK may play a role in regulating these events.

E. Inhibition of Tumor Cell Motility by FAK Antisense Compounds

Tumor cells interact with basement membranes in a manner fundamentally different from normal cells. The results presented above suggested that antisense attenuation of p125$^{FAK}$ expression might interrupt the ability of tumor cells to bind to their adjacent basement membrane, an initial requirement in the sequence of events leading to invasion. A subsequent step in the invasion process involves alterations in cellular motility which allow cells to actually propel themselves across the basement membrane and enter the interstitial stroma. To assess the role of FAK in these events, we used an in vitro cell invasion assay and determined the changes in the migration patterns of C8161 cells, which are known to the highly invasive, after attenuation of p125$^{FAK}$ expression.

The invasion assay allowed measurement of the invasive potential of cells through a reconstituted basement membrane in a modified Boyden chamber. Biocoat Matrigel Invasion Chambers (Becton Dickinson) were rehydrated over 2 hours by adding 2 ml of warm Opti-Mem and placed into individual wells of Falcon six-well culture plates. Conditioned medium was obtained by incubating human fibroblasts for 24 hours in Opti-Mem. This medium was used as a source of chemoattractants and was placed in the lower compartment of the Boyden chambers. $2\times10^5$ C8161 cells pre-treated with FAK antisense or 5 bp missense oligonucleosides were suspended in Opti-Mem containing 10% FCS and added to the rehydrated upper chambers. Assays were carried out at 37° C. in 5% $CO_2$. At the end of the incubation (about 24 hours), the cells on the upper surface of the filter were completely removed by wiping with a cotton swab under direct microscopic visualization. The filters were fixed in methanol and stained with hematoxylin and eosin. Cells from various areas of the lower surface were counted to correlate cell invasion of the reconstituted basement membrane. Each assay was performed in triplicate.

Figure 8:
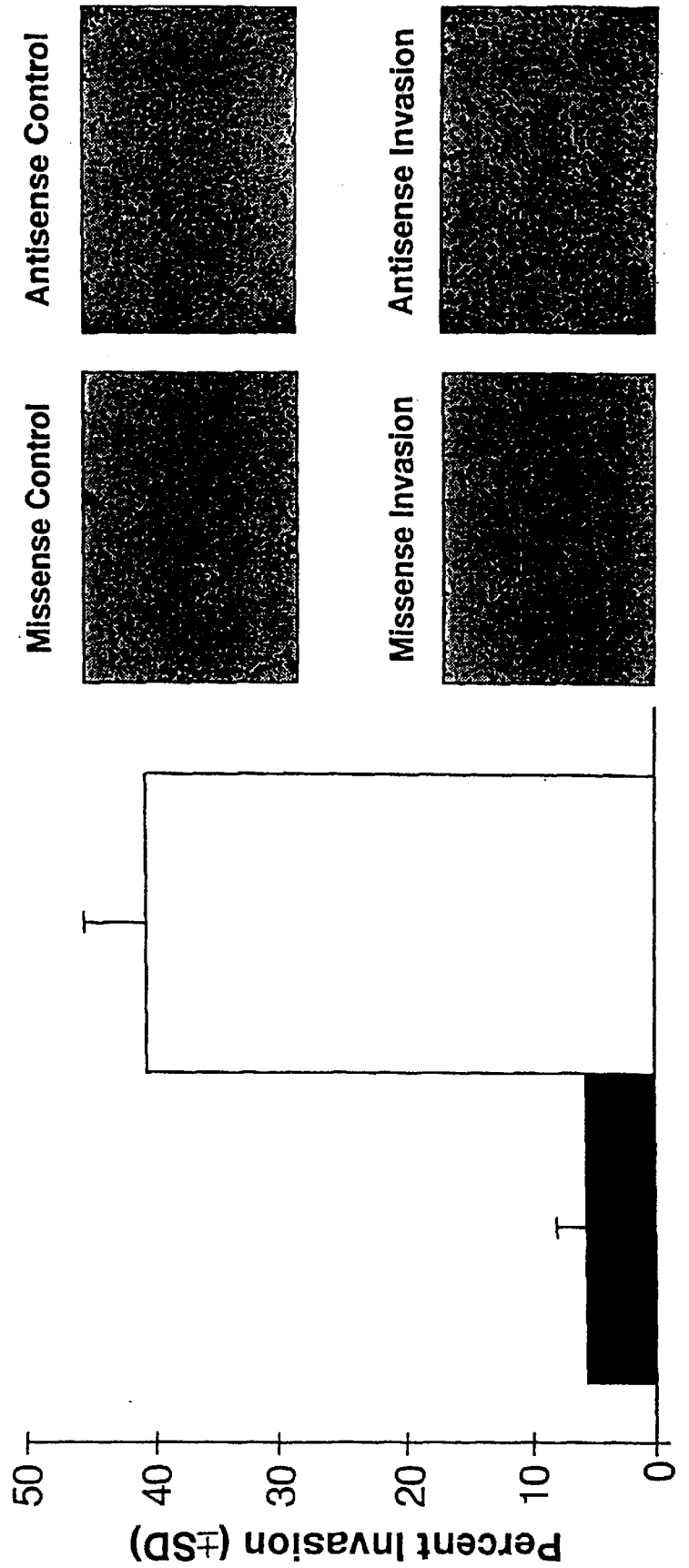
FIG. 8 is a bar graph (left) showing inhibition of C8161 cell invasive potential by an antisense compound of the invention compared to a 5 bp missense control, and depictions of stained cell filters (right).

As shown in FIG. 8, the antisense treated cells demonstrated a dramatically lower invasive potential (5.8±4.3%) compared to the missense treated control (40.6±5.2%). An emerging theme in the study of tumor invasion is that, in addition to unrestrained growth, tumor cells display an imbalanced regulation of motility and proteolysis. These in vitro results suggest that FAK may be closely involved in the former of these two critical processes.

F. Inhibition of Anchorage-Independent Growth Properties by FAK Antisense Compounds In addition to motility changes, invasive and metastatic cells develop enhanced anchorage-independent growth properties. This phenomenon is most apparent in human malignancy during the events leading to tumor dissemination in processes such as carcinomatosis, as well as in tumor cell colony formation in metastatic target organs. We assessed the anchorage-independent growth properties in FAK antisense treated cells by measuring their ability to form colonies in soft agar.

Two different tumor cell lines (C8161 and RD) were used in these studies. Oligonucleoside treated cells were seeded at a density of $5\times10^4$ cells per plate in a 0.33% top agarose layer in RPMI-1640 supplemented with 10% fetal bovine serum. The semisolid cell containing agar was layered onto 0.5% hard agar and incubated on scored tissue culture dishes (60 mm in diameter) in a humidified, 5% $CO_2$ atmosphere at 37° C. The dishes were fed once every several days with 1.0 ml of 1X medium. Colony formation efficiency was determined after two weeks in triplicate, blinded fashion by phase contrast microscopy counting all colonies larger than 70nmm in diameter.

The results of these studies are shown in Table 3, wherein the values represent the number of colonies in soft agar along with a calculated colony forming efficiency (total colonies per plate/total cells per plate, times 100). Following specific attenuation of FAK expression using either the FAK1AS (SEQ ID NO:4) or FAK2AS (SEQ ID NO:5) antisense compounds, a marked reduction in colony formation in soft agar was seen compared to cells treated with the control missense oligonucleoside MSN2 (SEQ ID NO:7).

After two weeks of culture there was a 81% reduction in colony formation efficiency in the C8161 cells treated with a FAK antisense oligonucleosides and a 85% reduction in colony formation efficiency in the RD cells treated with FAK antisense compared to cells treated with missense oligonucleosides. These results confirm that the loss of adhesion seen in cells after FAK antisense treatment is associated with reduced anchorage-independent growth.

TABLE 3

ANCHORAGE-INDEPENDENT GROWTH OF FAK ANTISENSE TREATED CELLS

| C8161 | Total # Colonies | Colony Forming Efficiency |
|---|---|---|
| MSN2 | 29,818 (±907) | 59.6 |
| FAK2AS | 5,759 (±571) | 11.5 |
| RD | Total # Colonies | Colony Forming Efficiency |
| MSN2 | 10,205 (±2586) | 20.4 |
| FAK2AS | 1,544 (±630) | 3.1 |

G. Inhibition of Tumor Formation in Nude Mice by FAK Antisense Compounds

The ability of FAK antisense compounds to inhibit tumor formation in athymic nude mice was also tested. Four-week old female athymic nude mice (Harlan Sprague-Dawley) were used in this study. Animals were maintained under the guidelines of the National Institutes of Health and The University of North Carolina School of Medicine. Mice were injected s.c. in the dorsolateral left flank with cells (RD or C8161, $2\times10^6$) suspended in HBSS. Prior to injection the cells were either treated with FAK antisense (FAK1AS or FAK2AS) or missense control (MSN2) as previously described. Tumor growth was monitored serially beginning several days after injection. Two perpendicular measurements of the diameter of any palpable nodule were obtained, and an estimated volume was calculated as $1w^2/2$. The animal was sacrificed at the end of the experiment and examined for any intrusion of tumor through the body wall or evidence of metastases to various body organs. The tumors were removed and protein extracted for FAK analysis.

Figure 9:
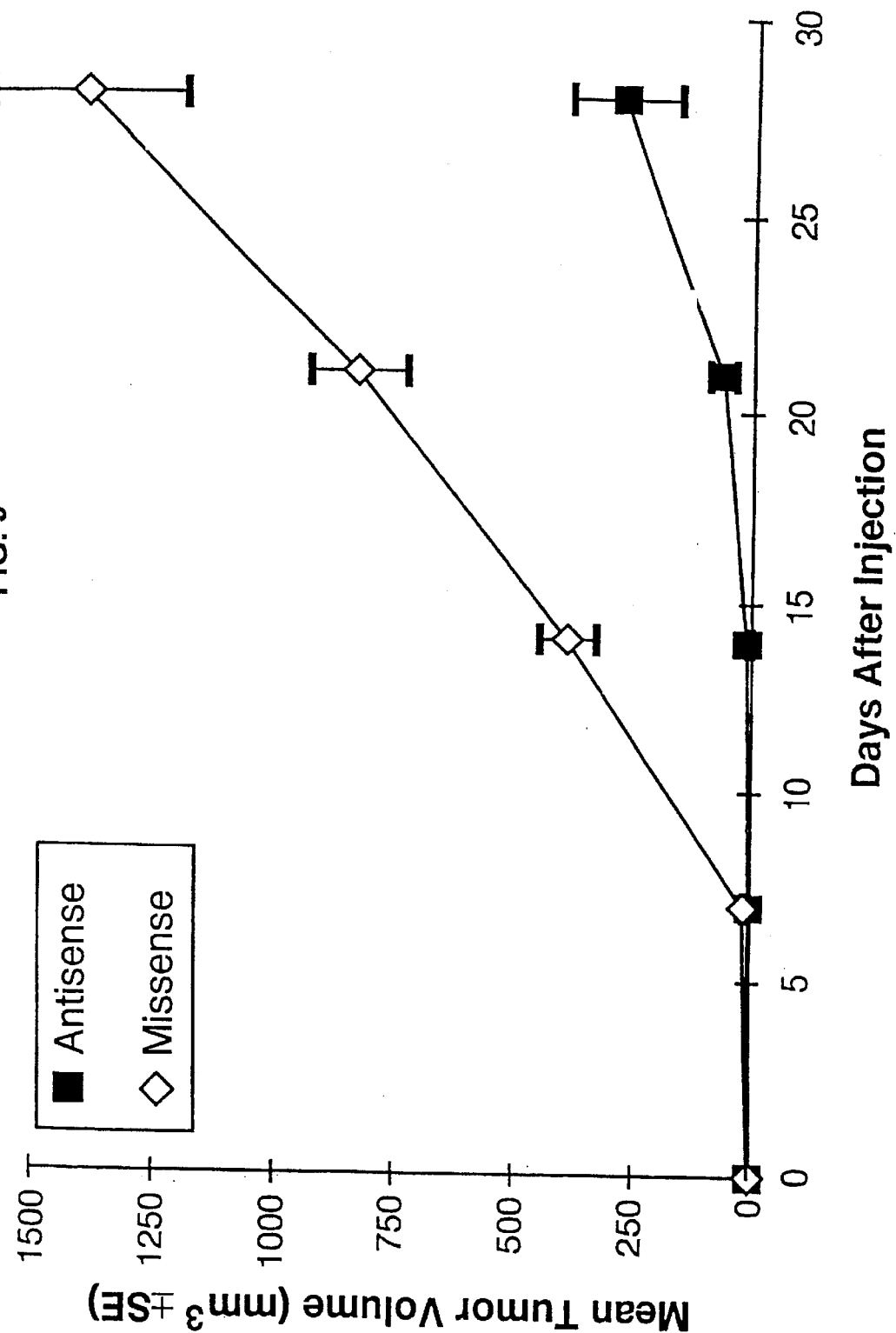
FIG. 9 is a graph of mean tumor volume over time, showing reduced tumor growth in athymic nude mice receiving cancer cells treated with an FAK antisense compound of the invention as compared to cells treated with a 5 bp missense compound.

As shown in FIG. 9, there was a significant lag time (almost 2 weeks) in the development of tumors using both RD and C8161 treated cells. This was surprising since related studies (see FIG. 4) had shown that such cells regain their FAK expression capability after seventy-two hours.

The foregoing results show that increased levels of p125$^{FAK}$ are associated with tumor invasion and metastasis and that disruption of this pathway by attenuating p125$^{FAK}$ expression with FAK antisense oligonucleosides significantly inhibits cellular adhesion, motility and anchorage independence. This data also points to FAK as a mediator of the processes which are downstream from other signaling molecules such as c-src and fyn.

Although the present invention has been described in some detail by way of illustration and example for purposes of clarity of understanding, it will be readily apparent to those of ordinary skill in the art in light of the teachings of this invention that various changes and modifications may be made thereto, and various equivalents used, without departing from the spirit or scope of the claims. Therefore, the foregoing description should not be construed to limit the scope of the present invention, which is set forth in the appended claims.

What is claimed:

1. An oligonucleoside compound comprising from about 6 to about 40 linked nucleosides in a sequence that is complementary to at least a portion of a focal adhesion kinase mRNA selected from the group consisting of 5'- . . . UUU GAU AAG GAA UCG UUC AAG UGU . . . -3' (SEQ ID NO:9); and 5'. . . CUU GGU UCA AGC UCG AUU AU . . . -3' (SEQ ID NO:10), wherein said oligonucleoside inhibits expression of human focal adhesion kinase protein.

2. An oligonucleoside compound of claim 1 wherein at least one of the internucleoside linkage structures in the compound is a non-phosphodiester linkage that is resistant to degradation by an endogenous cellular nuclease.

3. The oligonucleoside compound of claim 1 wherein said at least one non-phosphodiester linkage is a linkage selected from the group consisting of phosphorothioate, phosphorodithioate, alkyl- or arylphosphonate, phosphoramidate, phosphotriester, alkyl- or arylphosphonothioate, aminoalkylphosphonate, aminoalkylphosphonothioate, phosphorofluoridate, boranophosphate, silyl, formacetal, thioformacetal, morpholino, and peptide-based linkages.

4. The oligonucleoside compound of claim 1 comprising at least one phosphorothioate linkage.

5. The oligonucleoside compound of claim 1 comprising a plurality of phosphorothioate linkage.

6. An oligonucleoside compound comprising an oligonucleoside compound of SEQ ID NO: 4, wherein said oligonucleoside inhibits expression of a humnan focal adhesion kinase mRNA.

7. The oligonucleoside compound of claim 6 comprising at least one phosphorothioate linkage.

8. The oligonucleoside compound of claim 7 comprising a plurality of phosphorothioate linkages.

9. An oligonucleoside compound comprising an oligonucleoside compound of SEQ ID NO: 5, wherein said oligonucleoside inhibits expression of a human focal adhesion kinase mDNA.

10. An oligonucleoside compound of claim 6 wherein at least one of the internucleoside linkage structures in the compound is a non-phosphodiester linkage that is resistant to degradation by an endogenoous cellular nuclease.

11. The oligonucleoside compound of claim 10 wherein said at least one non-phosphodiester linkage is a linkage selected from the group consisting of phosphorothioate, phosphorodithioate, alkyl- or arylphosphonate, phosphoramidate, phosphotriester, alkyl- or arylphosphonotfhioate, anminoalkylphosphonate, aminoalkylphosphonothioate, phosphorofluoridate, boranophosphate, silyl, formacetal, thiofonnacetal, morpholino, and peptide-based linkages.

12. An oligonucleoside compound of claim 9 wherein at least one of the intemucleoside linkage structures in the compound is a non-phosphodiester linkage that is resistant to degradation by an endogenous cellular nuclease.

13. The oligonucleoside compound of claim 12 wherein said at least one non-phosphodiester linkage is a linkage selected from the group consisting of phosphorothioate, phosphorodithioate, alkyl- or arylphosphonate, phosphoramidate, phosphotriester, alkyl- or arylphosphonotiioate, aminoalkylphosphonate, aminoalkylphosphonothioate, phosphorofluoridate, boranophosphate, silyl, formacetal, thioformacetal, morpholinio, and peptide-based linkages.

14. The oligonucleoside compound of claim 9 comprising at least one phosphorothioate linkage.

15. The oligonucleoside compound of claim 14 comprising a plurality of phosphorothioate linkages.

* * * * *

UNITED STATES PATENT AND TRADEMARK OFFICE
CERTIFICATE OF CORRECTION

PATENT NO.   : 6,015,893
DATED        : January 18, 2000
INVENTOR(S)  : Cance et al.

It is certified that error appears in the above-identified patent and that said Letters Patent is hereby corrected as shown below:

Title page,
Item [56], References Cited, OTHER PUBLICATIONS, "Guan, et al." reference should read as follows: -- Guan, et al., "Fibronectin/integrin interaction induces tyrosine phosphorylation of a 120-kDa protein", *cell Regulation* 2:951-964 (Nov. 1991). --

Column 23,
Lines 1-11, claim 4 should read as follows:
    4. The connector of claim 1, the connector further including:
    a first resistive element having a resistance detectable at the terminal of the power supply for programming the power supply to apply a set voltage to the portable appliance; and
    a second resistive element having a resistance detectable at the terminal of the power supply for programming the power supply to apply a set current to the portable appliance.

Column 39,
Line 20, should read as follows: -- arylphosphonotfhioate, aminoalkylphosphonate, --

Column 40,
Line 4, should read as follows: -- least one of the internucleoside linkage structures in the --
Line 12, should read as follows: -- arylphosphonotioate, aminoalkylphosphonate, --

Signed and Sealed this

Ninth Day of March, 2004

JON W. DUDAS
*Acting Director of the United States Patent and Trademark Office*

SEQUENCE LISTING

<160> NUMBER OF SEQ ID NOS: 15

<210> SEQ ID NO 1
<211> LENGTH: 1052
<212> TYPE: PRT
<213> ORGANISM: Homo sapiens

<400> SEQUENCE: 1

```
Met Ala Ala Tyr Leu Asp Pro Asn Leu Asn His Thr Pro Asn Ser
 1               5                  10                  15

Ser Thr Lys Thr His Leu Gly Thr Gly Met Glu Arg Ser Pro Gly Ala
             20                  25                  30

Met Glu Arg Val Leu Lys Val Phe His His Phe Glu Ser Ser Ser Glu
         35                  40                  45

Pro Thr Thr Trp Ala Ser Ile Ile Arg His Gly Asp Ala Thr Asp Val
     50                  55                  60

Arg Gly Ile Ile Gln Lys Ile Val Asp Ser His Lys Val Lys His Val
 65                  70                  75                  80

Ala Cys Tyr Gly Phe Arg Leu Ser His Leu Arg Ser Glu Glu Val His
                 85                  90                  95

Trp Leu His Val Asp Met Gly Val Ser Ser Val Arg Glu Lys Tyr Glu
                100                 105                 110

Leu Ala His Pro Pro Glu Glu Trp Lys Tyr Glu Leu Arg Ile Arg Tyr
            115                 120                 125

Leu Pro Lys Gly Phe Leu Asn Gln Phe Thr Glu Asp Lys Pro Thr Leu
        130                 135                 140

Asn Phe Phe Tyr Gln Gln Val Lys Ser Asp Tyr Met Gln Glu Ile Ala
145                 150                 155                 160

Asp Gln Val Asp Gln Glu Ile Ala Leu Lys Leu Gly Cys Leu Glu Ile
                165                 170                 175

Arg Arg Ser Tyr Trp Glu Met Arg Gly Asn Ala Leu Glu Lys Lys Ser
                180                 185                 190

Asn Tyr Glu Val Leu Glu Lys Asp Val Gly Leu Lys Arg Phe Phe Pro
            195                 200                 205

Lys Ser Leu Leu Asp Ser Val Lys Ala Lys Thr Leu Arg Lys Leu Ile
        210                 215                 220

Gln Gln Thr Phe Arg Gln Phe Ala Asn Leu Asn Arg Glu Glu Ser Ile
225                 230                 235                 240

Leu Lys Phe Phe Glu Ile Leu Ser Pro Val Tyr Arg Phe Asp Lys Glu
                245                 250                 255

Cys Phe Lys Cys Ala Leu Gly Ser Ser Trp Ile Ile Ser Val Glu Leu
                260                 265                 270

Ala Ile Gly Pro Glu Glu Gly Ile Ser Tyr Leu Thr Asp Lys Gly Cys
            275                 280                 285

Asn Pro Thr His Leu Ala Asp Phe Thr Gln Val Gln Thr Ile Gln Tyr
        290                 295                 300

Ser Asn Ser Glu Asp Lys Asp Arg Lys Gly Met Leu Gln Leu Lys Ile
305                 310                 315                 320

Ala Gly Ala Pro Glu Pro Leu Thr Val Thr Ala Pro Ser Leu Thr Ile
                325                 330                 335

Ala Glu Asn Met Ala Asp Leu Ile Asp Gly Tyr Cys Arg Leu Val Asn
                340                 345                 350

Gly Thr Ser Gln Ser Phe Ile Ile Arg Pro Gln Lys Glu Gly Glu Arg
            355                 360                 365
```

```
Ala Leu Pro Ser Ile Pro Lys Leu Ala Asn Ser Glu Lys Gln Gly Met
    370                 375                 380

Arg Thr His Ala Val Ser Val Ser Glu Thr Asp Asp Tyr Ala Glu Ile
385                 390                 395                 400

Ile Asp Glu Glu Asp Thr Tyr Thr Met Pro Ser Thr Arg Asp Tyr Glu
                405                 410                 415

Ile Gln Arg Glu Arg Ile Glu Leu Gly Arg Cys Ile Gly Glu Gly Gln
            420                 425                 430

Phe Gly Asp Val His Gln Gly Ile Tyr Met Ser Pro Glu Asn Pro Ala
        435                 440                 445

Leu Ala Val Ala Ile Lys Thr Cys Lys Asn Cys Thr Ser Asp Ser Val
    450                 455                 460

Arg Glu Lys Phe Leu Gln Glu Ala Leu Thr Met Arg Gln Phe Asp His
465                 470                 475                 480

Pro His Ile Val Lys Leu Ile Gly Val Ile Thr Glu Asn Pro Val Trp
                485                 490                 495

Ile Ile Met Glu Leu Cys Thr Leu Gly Glu Leu Arg Ser Phe Leu Gln
            500                 505                 510

Val Arg Lys Tyr Ser Leu Asp Leu Ala Ser Leu Ile Leu Tyr Ala Tyr
        515                 520                 525

Gln Leu Ser Thr Ala Leu Ala Tyr Leu Glu Ser Lys Arg Phe Val His
    530                 535                 540

Arg Asp Ile Ala Ala Arg Asn Val Leu Val Ser Ser Asn Asp Cys Val
545                 550                 555                 560

Lys Leu Gly Asp Phe Gly Leu Ser Arg Tyr Met Glu Asp Ser Thr Tyr
                565                 570                 575

Tyr Lys Ala Ser Lys Gly Lys Leu Pro Ile Lys Trp Met Ala Pro Glu
            580                 585                 590

Ser Ile Asn Phe Arg Arg Phe Thr Ser Ala Ser Asp Val Trp Met Phe
        595                 600                 605

Gly Val Cys Met Trp Glu Ile Leu Met His Gly Val Lys Pro Phe Gln
    610                 615                 620

Gly Val Lys Asn Asn Asp Val Ile Gly Arg Ile Glu Asn Gly Glu Arg
625                 630                 635                 640

Leu Pro Met Pro Pro Asn Cys Pro Pro Thr Leu Tyr Ser Leu Met Thr
                645                 650                 655

Lys Cys Trp Ala Tyr Asp Pro Ser Arg Arg Pro Arg Phe Thr Glu Leu
            660                 665                 670

Lys Ala Gln Leu Ser Thr Ile Leu Glu Glu Glu Lys Ala Gln Gln Glu
        675                 680                 685

Glu Arg Met Arg Met Glu Ser Arg Arg Gln Ala Thr Val Ser Trp Asp
    690                 695                 700

Ser Gly Gly Ser Asp Glu Ala Pro Pro Lys Pro Ser Arg Pro Gly Tyr
705                 710                 715                 720

Pro Ser Pro Arg Ser Ser Glu Gly Phe Tyr Pro Ser Pro Gln His Met
                725                 730                 735

Val Gln Thr Asn His Tyr Gln Val Ser Gly Tyr Pro Gly Ser His Gly
            740                 745                 750

Ile Thr Ala Met Ala Gly Ser Ile Tyr Pro Gly Gln Ala Ser Leu Leu
        755                 760                 765

Asp Gln Thr Asp Ser Trp Asn His Arg Pro Gln Glu Ile Ala Met Trp
    770                 775                 780

Gln Pro Asn Val Glu Asp Ser Thr Val Leu Asp Leu Arg Gly Ile Gly
```

-continued

```
            785                 790                 795                 800
Gln Val Leu Pro Thr His Leu Met Glu Glu Arg Leu Ile Arg Gln Gln
                    805                 810                 815
Gln Glu Met Glu Glu Asp Gln Arg Trp Leu Glu Lys Glu Glu Arg Phe
            820                 825                 830
Leu Lys Pro Asp Val Arg Leu Ser Arg Gly Ser Ile Asp Arg Glu Asp
            835                 840                 845
Gly Ser Leu Gln Gly Pro Ile Gly Asn Gln His Ile Tyr Gln Pro Val
            850                 855                 860
Gly Lys Pro Asp Pro Ala Ala Pro Pro Lys Lys Pro Pro Arg Pro Gly
865                 870                 875                 880
Ala Pro Gly His Leu Gly Ser Leu Ala Ser Leu Ser Ser Pro Ala Asp
                    885                 890                 895
Ser Tyr Asn Glu Gly Val Lys Leu Gln Pro Gln Glu Ile Ser Pro Pro
                900                 905                 910
Pro Thr Ala Asn Leu Asp Arg Ser Asn Asp Lys Val Tyr Glu Asn Val
                    915                 920                 925
Thr Gly Leu Val Lys Ala Val Ile Glu Met Ser Ser Lys Ile Gln Pro
                    930                 935                 940
Ala Pro Pro Glu Glu Tyr Val Pro Met Val Lys Glu Val Gly Leu Ala
945                 950                 955                 960
Leu Arg Thr Leu Leu Ala Thr Val Asp Glu Thr Ile Pro Leu Leu Pro
                    965                 970                 975
Ala Ser Thr His Arg Glu Ile Glu Met Ala Gln Lys Leu Leu Asn Ser
                    980                 985                 990
Asp Leu Gly Glu Leu Ile Asn Lys Met Lys Leu Ala Gln Gln Tyr Val
                    995                 1000                1005
Met Thr Ser Leu Gln Gln Glu Tyr Lys Lys Gln Met Leu Thr Ala Ala
            1010                1015                1020
His Ala Leu Ala Val Asp Ala Lys Asn Leu Leu Asp Val Ile Asp Gln
1025                1030                1035                1040
Ala Arg Leu Lys Met Leu Gly Gln Thr Arg Pro His
                    1045                1050

<210> SEQ ID NO 2
<211> LENGTH: 1052
<212> TYPE: PRT
<213> ORGANISM: Mus musculus

<400> SEQUENCE: 2

Met Ala Ala Ala Tyr Leu Asp Pro Asn Leu Asn His Thr Pro Ser Ser
1               5                   10                  15
Ser Thr Lys Thr His Leu Gly Thr Gly Met Glu Arg Ser Pro Gly Ala
                    20                  25                  30
Met Glu Arg Val Leu Lys Val Phe His His Phe Glu Ser Ser Ser Glu
            35                  40                  45
Pro Thr Thr Trp Ala Ser Ile Ile Arg His Gly Asp Ala Thr Asp Val
            50                  55                  60
Arg Gly Ile Ile Gln Lys Ile Val Asp Ser His Lys Val Lys His Val
65                  70                  75                  80
Ala Cys Tyr Gly Phe Arg Leu Ser His Leu Arg Ser Glu Glu Val His
                    85                  90                  95
Trp Leu His Val Asp Met Gly Val Ser Ser Val Arg Glu Lys Tyr Glu
                    100                 105                 110
Leu Ala His Pro Pro Glu Glu Trp Lys Tyr Glu Leu Arg Ile Arg Tyr
```

-continued

```
                115                 120                 125
Leu Pro Lys Gly Phe Leu Asn Gln Phe Thr Glu Asp Lys Pro Thr Leu
    130                 135                 140
Asn Phe Phe Tyr Gln Gln Val Lys Ser Asp Tyr Met Gln Glu Ile Ala
145                 150                 155                 160
Asp Gln Val Asp Gln Glu Ile Ala Leu Lys Leu Gly Cys Leu Glu Ile
                165                 170                 175
Arg Arg Ser Tyr Trp Glu Met Arg Gly Asn Ala Leu Glu Lys Lys Ser
                180                 185                 190
Asn Tyr Glu Val Leu Glu Lys Asp Val Gly Leu Lys Arg Phe Phe Pro
            195                 200                 205
Lys Ser Leu Leu Asp Ser Val Lys Ala Lys Thr Leu Arg Lys Leu Ile
    210                 215                 220
Gln Gln Thr Phe Arg Gln Phe Ala Asn Leu Asn Arg Glu Glu Ser Ile
225                 230                 235                 240
Leu Lys Phe Phe Glu Ile Leu Ser Pro Val Tyr Arg Phe Asp Lys Glu
                245                 250                 255
Cys Phe Lys Cys Ala Leu Gly Ser Ser Trp Ile Ile Ser Val Glu Leu
                260                 265                 270
Ala Ile Gly Pro Glu Glu Gly Ile Ser Tyr Leu Thr Asp Lys Gly Cys
            275                 280                 285
Asn Pro Thr His Leu Ala Asp Phe Asn Gln Val Gln Thr Ile Gln Tyr
    290                 295                 300
Ser Asn Ser Glu Asp Lys Asp Arg Lys Gly Met Leu Gln Leu Lys Ile
305                 310                 315                 320
Ala Gly Ala Pro Glu Pro Leu Thr Val Thr Ala Pro Ser Leu Thr Ile
                325                 330                 335
Ala Glu Asn Met Ala Asp Leu Ile Asp Gly Tyr Cys Arg Leu Val Asn
                340                 345                 350
Gly Ala Thr Gln Ser Phe Ile Ile Arg Pro Gln Lys Glu Gly Glu Arg
            355                 360                 365
Ala Leu Pro Ser Ile Pro Lys Leu Ala Asn Ser Glu Lys Gln Gly Met
    370                 375                 380
Arg Thr His Ala Val Ser Val Ser Glu Thr Asp Asp Tyr Ala Glu Ile
385                 390                 395                 400
Ile Asp Glu Glu Asp Thr Tyr Thr Met Pro Ser Thr Arg Asp Tyr Glu
                405                 410                 415
Ile Gln Arg Glu Arg Ile Glu Leu Gly Arg Cys Ile Gly Glu Gly Gln
                420                 425                 430
Phe Gly Asp Val His Gln Gly Val Tyr Leu Ser Pro Glu Asn Pro Ala
            435                 440                 445
Leu Ala Val Ala Ile Lys Thr Cys Lys Asn Cys Thr Ser Asp Ser Val
    450                 455                 460
Arg Glu Lys Phe Leu Gln Glu Ala Leu Thr Met Arg Gln Phe Asp His
465                 470                 475                 480
Pro His Ile Val Lys Leu Ile Gly Val Ile Thr Glu Asn Pro Val Trp
                485                 490                 495
Ile Ile Met Glu Leu Cys Thr Leu Gly Glu Leu Arg Ser Phe Leu Gln
                500                 505                 510
Val Arg Lys Tyr Ser Leu Asp Leu Ala Ser Leu Ile Leu Tyr Ala Tyr
            515                 520                 525
Gln Leu Ser Thr Ala Leu Ala Tyr Leu Glu Ser Lys Arg Phe Val His
    530                 535                 540
```

-continued

```
Arg Asp Ile Ala Ala Arg Asn Val Leu Val Ser Ser Asn Asp Cys Val
545                 550                 555                 560

Lys Leu Gly Asp Phe Gly Leu Ser Arg Tyr Met Glu Asp Ser Thr Tyr
                565                 570                 575

Tyr Lys Ala Ser Lys Gly Lys Leu Pro Ile Lys Trp Met Ala Pro Glu
                580                 585                 590

Ser Ile Asn Phe Arg Arg Phe Thr Ser Ala Ser Asp Val Trp Met Phe
            595                 600                 605

Gly Val Cys Met Trp Glu Ile Leu Met His Gly Val Lys Pro Phe Gln
610                 615                 620

Gly Val Lys Asn Asn Asp Val Ile Gly Arg Ile Glu Asn Gly Glu Arg
625                 630                 635                 640

Leu Pro Met Pro Pro Asn Cys Pro Pro Thr Leu Tyr Ser Leu Met Thr
                645                 650                 655

Lys Cys Trp Ala Tyr Asp Pro Ser Arg Arg Pro Arg Phe Thr Glu Leu
                660                 665                 670

Lys Ala Gln Leu Ser Thr Ile Leu Glu Glu Glu Lys Val Gln Gln Glu
                675                 680                 685

Glu Arg Met Arg Met Glu Ser Arg Arg Gln Ala Thr Val Ser Trp Asp
            690                 695                 700

Ser Gly Gly Ser Asp Glu Ala Pro Pro Lys Pro Ser Arg Pro Gly Tyr
705                 710                 715                 720

Pro Ser Pro Arg Ser Ser Glu Gly Phe Tyr Pro Ser Pro Gln His Met
                725                 730                 735

Val Gln Thr Asn His Tyr Gln Val Ser Gly Tyr Pro Gly Ser His Gly
                740                 745                 750

Ile Pro Ala Met Ala Gly Ser Ile Tyr Gln Gly Gln Ala Ser Leu Leu
                755                 760                 765

Asp Gln Thr Glu Leu Trp Asn His Arg Pro Gln Glu Met Ser Met Trp
770                 775                 780

Gln Pro Ser Val Glu Asp Ser Ala Ala Leu Asp Leu Arg Gly Met Gly
785                 790                 795                 800

Gln Val Leu Pro Pro His Leu Met Glu Glu Arg Leu Ile Arg Gln Gln
                805                 810                 815

Gln Glu Met Glu Glu Asp Gln Arg Trp Leu Glu Lys Glu Glu Arg Phe
            820                 825                 830

Leu Lys Pro Asp Val Arg Leu Ser Arg Gly Ser Ile Asp Arg Glu Asp
            835                 840                 845

Gly Ser Phe Gln Gly Pro Thr Gly Asn Gln His Ile Tyr Gln Pro Val
850                 855                 860

Gly Lys Pro Asp Pro Ala Ala Pro Pro Lys Lys Pro Pro Arg Pro Gly
865                 870                 875                 880

Ala Pro Gly His Leu Ser Asn Leu Ser Ser Ile Ser Ser Pro Ala Asp
                885                 890                 895

Ser Tyr Asn Glu Gly Val Lys Leu Gln Pro Gln Glu Ile Ser Pro Pro
                900                 905                 910

Pro Thr Ala Asn Leu Asp Arg Ser Asn Asp Lys Val Tyr Glu Asn Val
                915                 920                 925

Thr Gly Leu Val Lys Ala Val Ile Glu Met Ser Ser Lys Ile Gln Pro
                930                 935                 940

Ala Pro Pro Glu Glu Tyr Val Pro Met Val Lys Glu Val Gly Leu Ala
945                 950                 955                 960

Leu Arg Thr Leu Leu Ala Thr Val Asp Glu Thr Ile Pro Ala Leu Pro
                965                 970                 975
```

-continued

```
Ala Ser Thr His Arg Glu Ile Glu Met Ala Gln Lys Leu Leu Asn Ser
            980                 985                 990

Asp Leu Gly Glu Leu Ile Ser Lys Met Lys Leu Ala Gln Gln Tyr Val
            995                 1000                1005

Met Thr Ser Leu Gln Gln Glu Tyr Lys Lys Gln Met Leu Thr Ala Ala
    1010                1015                1020

His Ala Leu Ala Val Asp Ala Lys Asn Leu Leu Asp Val Ile Asp Gln
1025                1030                1035                1040

Ala Arg Leu Lys Met Leu Gly Gln Thr Arg Pro His
                1045                1050

<210> SEQ ID NO 3
<211> LENGTH: 1053
<212> TYPE: PRT
<213> ORGANISM: Gallus sp.

<400> SEQUENCE: 3

Met Ala Ala Ala Tyr Leu Asp Pro Asn Leu Asn His Thr Pro Ser Ser
1               5                   10                  15

Ser Ala Lys Thr His Leu Gly Thr Gly Met Glu Arg Ser Pro Gly Ala
            20                  25                  30

Met Glu Arg Val Leu Lys Val Phe His Tyr Phe Glu Asn Ser Ser Glu
        35                  40                  45

Pro Thr Thr Trp Ala Ser Ile Ile Arg His Gly Asp Ala Thr Asp Val
    50                  55                  60

Arg Gly Ile Ile Gln Lys Ile Val Asp Cys His Lys Val Lys Asn Val
65                  70                  75                  80

Ala Cys Tyr Gly Leu Arg Leu Ser His Leu Gln Ser Glu Glu Val His
                85                  90                  95

Trp Leu His Leu Asp Met Gly Val Ser Asn Val Arg Glu Lys Phe Glu
            100                 105                 110

Leu Ala His Pro Pro Glu Glu Trp Lys Tyr Glu Leu Arg Ile Arg Tyr
        115                 120                 125

Leu Pro Lys Gly Phe Leu Asn Gln Phe Thr Glu Asp Lys Pro Thr Leu
    130                 135                 140

Asn Phe Phe Tyr Gln Gln Val Lys Asn Asp Tyr Met Leu Glu Ile Ala
145                 150                 155                 160

Asp Gln Val Asp Gln Glu Ile Ala Leu Lys Leu Gly Cys Leu Glu Ile
                165                 170                 175

Arg Arg Ser Tyr Gly Glu Met Arg Gly Asn Ala Leu Glu Lys Lys Ser
            180                 185                 190

Asn Tyr Glu Val Leu Glu Lys Asp Val Gly Leu Arg Arg Phe Phe Pro
        195                 200                 205

Lys Ser Leu Leu Asp Ser Val Lys Ala Lys Thr Leu Arg Lys Leu Ile
    210                 215                 220

Gln Gln Thr Phe Arg Gln Phe Ala Asn Leu Asn Arg Glu Glu Ser Ile
225                 230                 235                 240

Leu Lys Phe Phe Glu Ile Leu Ser Pro Val Tyr Arg Phe Asp Lys Glu
                245                 250                 255

Cys Phe Lys Cys Ala Leu Gly Ser Ser Trp Ile Ile Ser Val Glu Leu
            260                 265                 270

Ala Ile Gly Pro Glu Glu Gly Ile Ser Tyr Leu Thr Asp Lys Gly Ala
        275                 280                 285

Asn Pro Thr His Leu Ala Asp Phe Asn Gln Val Gln Thr Ile Gln Tyr
    290                 295                 300
```

-continued

```
Ser Asn Ser Glu Asp Lys Asp Arg Lys Gly Met Leu Gln Leu Lys Ile
305                 310                 315                 320

Ala Gly Ala Pro Glu Pro Leu Thr Val Thr Ala Pro Ser Leu Thr Ile
            325                 330                 335

Ala Glu Asn Met Ala Asp Leu Ile Asp Gly Tyr Cys Arg Leu Val Asn
                340                 345                 350

Gly Ala Thr Gln Ser Phe Ile Ile Arg Pro Gln Lys Glu Gly Glu Arg
            355                 360                 365

Ala Leu Pro Ser Ile Pro Lys Leu Ala Asn Asn Glu Lys Gln Gly Val
370                 375                 380

Arg Ser His Thr Val Ser Val Ser Glu Thr Asp Tyr Ala Glu Ile
385                 390                 395                 400

Ile Asp Glu Glu Asp Thr Tyr Thr Met Pro Ser Thr Arg Asp Tyr Glu
                405                 410                 415

Ile Gln Arg Glu Arg Ile Glu Leu Gly Arg Cys Ile Gly Glu Gly Gln
            420                 425                 430

Phe Gly Asp Val His Gln Gly Ile Tyr Met Ser Pro Glu Asn Pro Ala
            435                 440                 445

Met Ala Val Ala Ile Lys Thr Cys Lys Asn Cys Thr Ser Asp Ser Val
450                 455                 460

Arg Glu Lys Phe Leu Gln Glu Ala Leu Thr Met Arg Gln Phe Asp His
465                 470                 475                 480

Pro His Ile Val Lys Leu Ile Gly Val Ile Thr Glu Asn Pro Val Trp
                485                 490                 495

Ile Ile Met Glu Leu Cys Thr Leu Gly Glu Leu Arg Ser Phe Leu Gln
                500                 505                 510

Val Arg Lys Phe Ser Leu Asp Leu Ala Ser Leu Ile Leu Tyr Ala Tyr
            515                 520                 525

Gln Leu Ser Thr Ala Leu Ala Tyr Leu Glu Ser Lys Arg Phe Val His
            530                 535                 540

Arg Asp Ile Ala Ala Arg Asn Val Leu Val Ser Ala Thr Asp Cys Val
545                 550                 555                 560

Lys Leu Gly Asp Phe Gly Leu Ser Arg Tyr Met Glu Asp Ser Thr Tyr
            565                 570                 575

Tyr Lys Ala Ser Lys Gly Lys Leu Pro Ile Lys Trp Met Ala Pro Glu
            580                 585                 590

Ser Ile Asn Phe Arg Arg Phe Thr Ser Ala Ser Asp Val Trp Met Phe
            595                 600                 605

Gly Val Cys Met Trp Glu Ile Leu Met His Gly Val Lys Pro Phe Gln
            610                 615                 620

Gly Val Lys Asn Asn Asp Val Ile Gly Arg Ile Glu Asn Gly Glu Arg
625                 630                 635                 640

Leu Pro Met Pro Pro Asn Cys Pro Pro Thr Leu Tyr Ser Leu Met Thr
            645                 650                 655

Lys Cys Trp Ala Tyr Asp Pro Ser Arg Arg Pro Arg Phe Thr Glu Leu
            660                 665                 670

Lys Ala Gln Leu Ser Thr Ile Leu Glu Glu Glu Lys Leu Gln Gln Glu
            675                 680                 685

Glu Arg Met Arg Met Glu Ser Arg Arg Gln Val Thr Val Ser Trp Asp
            690                 695                 700

Ser Gly Gly Ser Asp Glu Ala Pro Pro Lys Pro Ser Arg Pro Gly Tyr
705                 710                 715                 720

Pro Ser Pro Arg Ser Ser Glu Gly Phe Tyr Pro Ser Pro Gln His Met
```

```
                       725                 730                 735
Val Gln Pro Asn His Tyr Gln Val Ser Gly Tyr Ser Gly Ser His Gly
                740                 745                 750

Ile Pro Ala Met Ala Gly Ser Ile Tyr Pro Gly Gln Ala Ser Leu Leu
            755                 760                 765

Asp Gln Thr Asp Ser Trp Asn His Arg Pro Gln Glu Val Ser Ala Trp
        770                 775                 780

Gln Pro Asn Met Glu Asp Ser Gly Thr Leu Asp Val Arg Gly Met Gly
785                 790                 795                 800

Gln Val Leu Pro Thr His Leu Met Glu Glu Arg Leu Ile Arg Gln Gln
                805                 810                 815

Gln Glu Met Glu Glu Asp Gln Arg Trp Leu Glu Lys Glu Glu Arg Phe
            820                 825                 830

Leu Val Met Lys Pro Asp Val Arg Leu Ser Arg Gly Ser Ile Glu Arg
        835                 840                 845

Glu Asp Gly Gly Leu Gln Gly Pro Ala Gly Asn Gln His Ile Tyr Gln
850                 855                 860

Pro Val Gly Lys Pro Asp His Ala Ala Pro Lys Lys Pro Pro Arg
865                 870                 875                 880

Pro Gly Ala Pro His Leu Gly Ser Leu Ala Ser Leu Asn Ser Pro Val
                885                 890                 895

Asp Ser Tyr Asn Glu Gly Val Lys Ile Lys Pro Gln Glu Ile Ser Pro
            900                 905                 910

Pro Pro Thr Ala Asn Leu Asp Arg Ser Asn Asp Lys Val Tyr Glu Asn
        915                 920                 925

Val Thr Gly Leu Val Lys Ala Val Ile Glu Met Ser Ser Lys Ile Gln
        930                 935                 940

Pro Ala Pro Pro Glu Glu Tyr Val Pro Met Val Lys Glu Val Gly Leu
945                 950                 955                 960

Ala Leu Arg Thr Leu Leu Ala Thr Val Asp Glu Ser Leu Pro Val Leu
                965                 970                 975

Pro Ala Ser Thr His Arg Glu Ile Glu Met Ala Gln Lys Leu Leu Asn
            980                 985                 990

Ser Asp Leu Ala Glu Leu Ile Asn Lys Met Lys Leu Ala Gln Gln Tyr
        995                 1000                1005

Val Met Thr Ser Leu Gln Gln Glu Tyr Lys Lys Gln Met Leu Thr Ala
    1010                1015                1020

Ala His Ala Leu Ala Val Asp Ala Lys Asn Leu Leu Asp Val Ile Asp
1025                1030                1035                1040

Gln Ala Arg Leu Lys Met Ile Ser Gln Ser Arg Pro His
                1045                1050

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: antisense
      oligonucleotide to FAK1

<400> SEQUENCE: 4
acacttgaag cattccttat caaa                                               24

<210> SEQ ID NO 5
<211> LENGTH: 20
<212> TYPE: DNA
<213> ORGANISM: Artificial Sequence
```

-continued

```
<220> FEATURE:
<223> OTHER INFORMATION: Description of Artificial Sequence: antisense
      oligonucleotide to FAK2

<400> SEQUENCE: 5
ataatccagc ttgaaccaag                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: antisense
      control sequences having base mismatches to FAK

<400> SEQUENCE: 6
ataatcgagc ttcaaccaag                                                    20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: antisense
      control sequence with base mismatches to FAK
      sequence

<400> SEQUENCE: 7
ataatcgacg ttcaagcaag                                                    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: nonsense
      control sequence derived from mouse wnt
      protooncogene

<400> SEQUENCE: 8
agcccgagca ggtggggctc                                                    20

<210> SEQ ID NO 9
<211> LENGTH: 24
<212> TYPE: RNA
<213> ORGANISM: Artificial Sequence
<220> FEATURE:
<223> OTHER INFORMATION: Description of Artificial Sequence: target
      region of focal adhesion kinase mRNA

<400> SEQUENCE: 9
uuugauaagg aaucguucaa gugu                                               24

<210> SEQ ID NO 10
<211> LENGTH: 20
<212> TYPE: RNA
<213> ORGANISM: Artificial Sequence
<220> FEATURE:
<223> OTHER INFORMATION: Description of Artificial Sequence: target
      region of focal adhesion kinase mRNA

<400> SEQUENCE: 10
cuugguucaa gcucgauuau                                                    20

<210> SEQ ID NO 11
<211> LENGTH: 21
<212> TYPE: RNA
<213> ORGANISM: Artificial Sequence
```

-continued

```
<220> FEATURE:
<223> OTHER INFORMATION: Description of Artificial Sequence: target
      region of focal adhesion kinase mRNA

<400> SEQUENCE: 11
cuugguucaa gcucgauuau u                                          21

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: portion of
      focal adhesion kinase  protein sequence

<400> SEQUENCE: 12

Phe Asp Lys Glu Cys Phe Lys Cys
 1               5

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: portion of
      focal adhesion kinase DNA sequence

<400> SEQUENCE: 13
aaactattcc ttagcaagtt caca                                       24

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: portion of
      focal adhesion kinase protein

<400> SEQUENCE: 14

Leu Gln Ser Ser Trp Ile Ile
 1               5

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: portion of
      focal adhesion kinase DNA sequence

<400> SEQUENCE: 15
gaaccaagtt cgacctaata                                            20
```